United States Patent
Lawson et al.

(10) Patent No.: US 8,465,744 B2
(45) Date of Patent: Jun. 18, 2013

(54) METHOD OF TREATING INFLAMMATION BY ADMINISTERING HUMAN IL-1B ANTIBODIES

(75) Inventors: Alastair David Griffiths Lawson, Slough (GB); Andrew George Popplewell, Slough (GB)

(73) Assignee: UCB Pharma S.A. (BE)

( * ) Notice: Subject to any disclaimer, the term of this patent is extended or adjusted under 35 U.S.C. 154(b) by 828 days.

(21) Appl. No.: 12/569,700

(22) Filed: Sep. 29, 2009

(65) Prior Publication Data
US 2010/0158913 A1 Jun. 24, 2010

Related U.S. Application Data

(62) Division of application No. 10/544,911, filed as application No. PCT/GB2004/000463 on Feb. 6, 2004, now Pat. No. 7,608,694.

(30) Foreign Application Priority Data

Feb. 13, 2003 (GB) .................................. 0303337.0

(51) Int. Cl.
*A61K 39/395* (2006.01)
(52) U.S. Cl.
USPC .................. 424/139.1; 424/141.1; 424/145.1
(58) Field of Classification Search
None
See application file for complete search history.

(56) References Cited

U.S. PATENT DOCUMENTS

| | | | |
|---|---|---|---|
| 4,935,343 A | 6/1990 | Allison et al. | |
| 5,681,933 A | 10/1997 | Auron et al. | |
| 2003/0026806 A1 | 2/2003 | Witte et al. | |

FOREIGN PATENT DOCUMENTS

| | | |
|---|---|---|
| EP | 0 392 745 B1 | 11/1994 |
| EP | 0 813 423 B1 | 7/2002 |
| EP | 0 948 544 B1 | 5/2003 |
| GB | 129105 | 7/1991 |
| WO | 86/01533 A1 | 3/1986 |
| WO | 89/00195 A1 | 1/1989 |
| WO | 89/01476 A1 | 3/1989 |
| WO | 91/09967 A1 | 7/1991 |
| WO | 92/22583 A2 | 12/1992 |
| WO | 93/06231 A1 | 4/1993 |
| WO | 95/01997 A | 1/1995 |
| WO | 98/20734 A1 | 5/1998 |
| WO | 99/15549 A | 4/1999 |
| WO | 01/53353 A3 | 7/2001 |
| WO | 02/16436 A3 | 2/2002 |
| WO | 03/010282 A | 2/2003 |
| WO | 2004/072116 A3 | 8/2004 |

OTHER PUBLICATIONS

Ezzell. Cancer "vaccines": an idea whose time has come? Journal of NIH Research, 1995. vol. 7, pp. 46-49.*
Forni, Lollini, Musiani, and Colombo. Immunoprevention of cancer: is the time ripe? Cancer Research, 2000. vol. 60, pp. 2571-2575.*
Donnelly. Cancer vaccine targets leukemia. Nature Medicine, 2003. vol. 11, pp. 1354-1356.*
De Gruijl and Curiel. Cancer vaccine strategies get bigger and better. Nature Medicine, 1999. vol. 5, pp. 1124-1125.*
Chatterjee, Foon, and Kohler. Idiotypic antibody immunotherapy of cancer. Cancer Immunology and Immunotherapy, 1994. vol. 38, pp. 75-82.*
Bodey, Bodey, Siegel, and Kaiser. Failure of cancer vaccines: the significant limitations of this approach to immunotheapy. Anticancer Research, 2000. vol. 20, pp. 2665-2676.*
Lee, Wang, Nielsen, Wunderlich, Migueles, Connors, Steinberg, Rosenberg, and Marincola. Increased vaccine specific T cell frequency after peptide based vaccination correlates with increased susceptibility to in vitro stimulation but does not lead to tumor regression. Journal of Immunology, 1999. vol. 163, pp. 6292-6300.*
Chapman, Andrew P., "PEGylated antibodies and antibody fragments for improved therapy: a review", Advanced Drug Delivery Reviews, 2002, 54(4), 531-545.
Davies, J et al., "Affinity improvement of single antibody VH domains: residues in all three hypervariable regions affect antigen binding", Immunotechnology, Elsevier Science Publishers BV, 1996, 169-179.
Chapman, A.P. et al., "Therapeutic antibody fragments with prolonged in vivo half-lives", Nature Biotechnology, 1999, vol. 17, 780-783.
Chothia, C. et al., "Canonical strucutres for the hypervariable regions of immunoglobulins", J. Mol. Biol., 1987, vol. 196, 901-917.
Crameri, A. et al., "DNA shuffling of a family of genes from diverse species accelerates directed evolution", Nature, 1998, vol. 391, 288-291.
Dinarello, C.A., "Biologic basis for interleukin-1 in disease", Blood, 1996, 87(6), 2095-2147.
Hieter, P.A. et al., "Evolution of human immunoglobulin K J region genes", J. Biol. Chem., 1982, 257(3), 1516-1522.
Low, N.M. et al., "Mimicking somatic hypermutation: affinity maturation of antibodies displayed on bacteriophage using a bacterial mutator strain", J. Mol. Biol., 1996, vol. 260, 359-368.
Marks, J.D. et al., "By-passing immunization: building high affinity human antibodies by chain shuffling", Bio. Technology, 1992, vol. 10, 779-783.
Movva, N.R. et al., "Amino acid sequence of the signal peptide of ompA protein, a major outer membrane protein of *Escherichia coli*", J. Biol. Chem., 1980, 255(1), 27-29.
Patten, P.A. et al., "Applications of DNA shuffling to pharmaceuticals and vaccines", Curr. Opin. Biotechnol., 1997, vol. 8, 724-733.
Ravetch, J.V. et al., "Structure of the human immunoglobulin u locus: characterization of embryonic and rearranged J and D genes", Cell, 1981, vol. 27, 583-591.
Reichmann, L. et al., "Reshaping human antibodies for therapy", Nature, 1998, vol. 332, 323-324.
Thompson, J. et al., "Affinity maturation of a high-affinity human monoclonal antibody against the third hypervariable loop of human immunodeficiency virus: use of phage display to improve affinity and broaden strain reactivity", J. Mol. Biol., 1996, vol. 256, 77-88.

(Continued)

*Primary Examiner* — Prema Mertz
(74) *Attorney, Agent, or Firm* — McDonnell Boehnen Hulbert & Berghoff

(57) ABSTRACT

The invention relates to an antibody molecule having specificity for antigenic determinants of IL-1β, therapeutic uses of the antibody molecule and methods for producing said antibody molecule.

20 Claims, 17 Drawing Sheets

OTHER PUBLICATIONS

Vaughan, T.J. et al., "Human antibodies by design", Nature Biotechnology, 1998, vol. 16, 535-539.

Wada, K.N. et al., "Codon usage tabulated from the GenBank genetic sequence data", Nucl. Acids Res., 1991, vol. 19, 1981-1986.

Yang, W.P. et al., "CDR walking mutagenesis for the affinity maturation of a potent human anti-HIV-1 antibody into the picomolar range", J. Mol. Biol., 1995, vol. 254, 392-403.

* cited by examiner

Figure 1a)

```
        10              20              30              40              50              60
ATG GAC TTT GGG CTC AGC TTG ATT TTC CTT GTC CTT ACT TTA AAA GGT GTG CAG
TAC CTG AAA CCC GAG TCG AAC TAA AAG GAA CAG GAA TGA AAT TTT CCA CAC GTC
 M   D   F   G   L   S   L   I   F   L   V   L   T   L   K   G   V   Q>

70              80              90             100             110
TGT GAT GTG CAG TTG GTG GAG TCT GGG GGA GGC TTA GTG AAG CCT GGA GGG TCC
ACA CTA CAC GTC AAC CAC CTC AGA CCC CCT CCG AAT CAC TTC GGA CCT CCC AGG
 C   D   V   Q   L   V   E   S   G   G   G   L   V   K   P   G   G   S>

120             130             140             150             160             170
CTG AAA CTC TCC TGT GCA GCC TCT GGA TTC GAT TTC AGT AGG TAT GAC ATG TCT
GAC TTT GAG AGG ACA CGT CGG AGA CCT AAG CTA AAG TCA TCC ATA CTG TAC AGA
 L   K   L   S   C   A   A   S   G   F   D   F   S   R   Y   D   M   S>

180             190             200             210             220
TGG GTT CGC CAG ACT CCG GAG AAG AGG CTG GAG TGG GTC GCA TAT ATT AGT AGT
ACC CAA GCG GTC TGA GGC CTC TTC TCC GAC CTC ACC CAG CGT ATA TAA TCA TCA
 W   V   R   Q   T   P   E   K   R   L   E   W   V   A   Y   I   S   S>

230             240             250             260             270
GGT GGT GGT AGC ACC TAC TTT CCA GAC ACT GTG AAG GGC CGA TTC ACC ATC TCC
CCA CCA CCA TCG TGG ATG AAA GGT CTG TGA CAC TTC CCG GCT AAG TGG TAG AGG
 G   G   G   S   T   Y   F   P   D   T   V   K   G   R   F   T   I   S>

280             290             300             310             320             330
AGA GAC AAT GCC AAG AAC ACC CTG TAC CTG CAA ATG AAC AAT CTG CAG TCT GAG
TCT CTG TTA CGG TTC TTG TGG GAC ATG GAC GTT TAC TTG TTA GAC GTC AGA CTC
 R   D   N   A   K   N   T   L   Y   L   Q   M   N   N   L   Q   S   E>

340             350             360             370             380
GAC ACA GCC ATG TTT TAC TGT GCA AGA CAG AAC AAG AAA TTA ACC TGG TTT GAT
CTG TGT CGG TAC AAA ATG ACA CGT TCT GTC TTG TTT AAT TGG ACC AAA CTA
 D   T   A   M   F   Y   C   A   R   Q   N   K   K   L   T   W   F   D>

390             400             410             420
TAC TGG GGC CAG GGG ACT CTG GTC ACT GTC TCT TCA
ATG ACC CCG GTC CCC TGA GAC CAG TGA CAG AGA AGT
 Y   W   G   Q   G   T   L   V   T   V   S   S>
```

Figure1b)

```
       10              20              30              40              50              60
ATG AGT GTG CTC ACT CAG GTC CTG GCG TTG CTG CTG CTG TGG CTT GCA GGT GCC
TAC TCA CAC GAG TGA GTC CAG GAC CGC AAC GAC GAC GAC ACC GAA CGT CCA CGG
 M   S   V   L   T   Q   V   L   A   L   L   L   L   W   L   A   G   A>

70              80              90             100             110
    AGA TGT GAC ATC CAG ATG ACT CAG TCT CCA GCC TCC CTA TCT GCA TCT GTG GGA
    TCT ACA CTG TAG GTC TAC TGA GTC AGA GGT CGG AGG GAT AGA CGT AGA CAC CCT
     R   C   D   I   Q   M   T   Q   S   P   A   S   L   S   A   S   V   G>

120             130             140             150             160             170
GAA ACT GTC ACC ATC ACA TGT CGA ACA AGT GGG AAT ATT CAC AAT TAT TTA ACA
CTT TGA CAG TGG TAG TGT ACA GCT TGT TCA CCC TTA TAA GTG TTA ATA AAT TGT
 E   T   V   T   I   T   C   R   T   S   G   N   I   H   N   Y   L   T>

180             190             200             210             220
    TGG TAT CAA CAG AAT TTG GGA AAA TCT CCT CAG CTC CTG GTC TAT AAT GCA AAA
    ACC ATA GTT GTC TTA AAC CCT TTT AGA GGA GTC GAG GAC CAG ATA TTA CGT TTT
     W   Y   Q   Q   N   L   G   K   S   P   Q   L   L   V   Y   N   A   K>

230             240             250             260             270
    ACC TTA GCA GAT GGT GTG CCA TCA AGG TTC AGT GGC AGT GGA TCA GGA ACA CAA
    TGG AAT CGT CTA CCA CAC GGT AGT TCC AAG TCA CCG TCA CCT AGT CCT TGT GTT
     T   L   A   D   G   V   P   S   R   F   S   G   S   G   S   G   T   Q>

280             290             300             310             320             330
TTT TCT CTC ACG ATC AAC AGC CTG CAG CCT GAA GAT TTT GGG AAT TAT TAC TGT
AAA AGA GAG TGC TAG TTG TCG GAC GTC GGA CTT CTA AAA CCC TTA ATA ATG ACA
 F   S   L   T   I   N   S   L   Q   P   E   D   F   G   N   Y   Y   C>

340             350             360             370             380
    CAA CAT TTT TGG AGT CTT CCA TTC ACG TTC GGC TCG GGG ACA AAG TTG GAA ATA
    GTT GTA AAA ACC TCA GAA GGT AAG TGC AAG CCG AGC CCC TGT TTC AAC CTT TAT
     Q   H   F   W   S   L   P   F   T   F   G   S   G   T   K   L   E   I>

390
AAA CGT
TTT GCA
 K   R>
```

Figure 3 a)

```
              1     5         10        15        20        25        30        35        40        45       50  a  55        60        65        70        75        80 abc 85        90        95        100       105  110
IC8 VH        DVQLVESGGGLVKPGGSLKLSCAASGFDFSRYDMSWVRQTPEKRLEWVAYISSGGGSTYFPDTVKGRFTISRDNAKNTLYLQMNNLQSEDTAMFYCARQNKKLTWFDYWGQGTLVTVSS
3.11(DP-35)   QVQLVESGGGLVKPGGSLRLSCAASGFTFSDYYMSWIRQAPGKGLEWVSYISSSGSTIYYADSVKGRFTISRDNAKNSLYLQMNSLRAEDTAVYYCAR           WGQGTLVTVSS
gH1           EVQLVESGGGLVQPGGSLRLSCAASGFDFSRYDMSWVRQAPGKGLEWVAYISSGGGSTYFPDTVKGRFTISRDNAKNTLYLQMNSLRAEDTAMYYCARQNKKLTWFDYWGQGTLVTVSS
gH2           EVQLVESGGGLVQPGGSLRLSCAASGFDFSRYDMSWVRQAPGKGLEWVAYISSGGGSTYFPDTVKGRFTISRDNAKNTLYLQMNSLRAEDTAMYYCARQNKKLTWFDYWGQGTLVTVSS
gH3           EVQLVESGGGLVQPGGSLRLSCAASGFDFSRYDMSWVRQAPGKRLEWVAYISSGGGSTYFPDTVKGRFTISRDNAKNTLYLQMNSLRAEDTAVYYCARQNKKLTWFDYWGQGTLVTVSS
``` b)

```
              1     5         10        15        20        25        30        35        40        45        50        55        60        65        70        75        80        85        90        95        100      105
IC8 VL        DIQMTQSPASLSASVGETVTITCRTSGNIHNYLTWYQQNLGKSPQLLVYNAKTLADGVPSRFSGSGSGTQFSLTINSLQPEDFGNYYCQHFWSLPFTFGSGTKLEIKR
O12(DPK9)     DIQMTQSPSSLSASVGDRVTITCRASQSISSYLNWYQQKPGKAPKLLIYAASSLQSGVPSRFSGSGSGTDFTLTISSLQPEDFATYYCQQSYSTP        FGQGTKVEIKR
IC8 gL1       DIQMTQSPSSLSASVGDRVTITCRTSGNIHNYLTWYQQKLGKAPQLLVYNAKTLADGVPSRFSGSGSGTQFTLTISSLQPEDFANYYCQHFWSLPFTFGQGTKVEIKR
IC8 gL2       DIQMTQSPSSLSASVGDRVTITCRTSGNIHNYLTWYQQKPGKAPQLLIYNAKTLADGVPSRFSGSGSGTQFTLTISSLQPEDFANYYCQHFWSLPFTFGQGTKVEIKR
IC8 gL3       DIQMTQSPSSLSASVGDRVTITCRTSGNIHNYLTWYQQKPGKAPQLLIYNAKTLADGVPSRFSGSGSGTQFTLTISSLQPEDFANYYCQHFWSLPFTFGQGTKVEIKR
```

Figure 4 a)

```
            10          20              30              40              50
GAATAAAAGCTTGCCGCCACC ATG GAC TTT GGG CTC AGC TTG ATT TTC CTT GTC CTT
CTTATTTTCGAACGGCGGTGG TAC CTG AAA CCC GAG TCG AAC TAA AAG GAA CAG GAA
                       M   D   F   G   L   S   L   I   F   L   V   L>

60              70              80              90              100             110
ACT TTA AAA GGT GTG CAG TGT GAG GTG CAG CTG GTC GAG TCT GGA GGC GGG CTT
TGA AAT TTT CCA CAC GTC ACA CTC CAC GTC GAC CAG CTC AGA CCT CCG CCC GAA
 T   L   K   G   V   Q   C   E   V   Q   L   V   E   S   G   G   G   L>

120             130             140             150             160
GTC CAG CCT GGA GGG AGC CTG CGT CTC TCT TGT GCA GCA AGC GGC TTC GAC TTT
CAG GTC GGA CCT CCC TCG GAC GCA GAG AGA ACA CGT CGT TCG CCG AAG CTG AAA
 V   Q   P   G   G   S   L   R   L   S   C   A   A   S   G   F   D   F>

170             180             190             200             210
TCC CGT TAC GAT ATG TCC TGG GTG CGG CAG GCA CCT GGG AAG CGC CTG GAG TGG
AGG GCA ATG CTA TAC AGG ACC CAC GCC GTC CGT GGA CCC TTC GCG GAC CTC ACC
 S   R   Y   D   M   S   W   V   R   Q   A   P   G   K   R   L   E   W>

220             230             240             250             260             270
GTG GCA TAC ATT AGC TCC GGA GGC GGC TCT ACA TAC TTC CCG GAC ACC GTC AAG
CAC CGT ATG TAA TCG AGG CCT CCG CCG AGA TGT ATG AAG GGC CTG TGG CAG TTC
 V   A   Y   I   S   S   G   G   G   S   T   Y   F   P   D   T   V   K>

280             290             300             310             320
GGC CGT TTC ACC ATT TCC CGG GAC AAT GCA AAG AAT ACC CTT TAC CTC CAG ATG
CCG GCA AAG TGG TAA AGG GCC CTG TTA CGT TTC TTA TGG GAA ATG GAG GTC TAC
 G   R   F   T   I   S   R   D   N   A   K   N   T   L   Y   L   Q   M>

330             340             350             360             370             380
AAC TCT CTC CGC GCA GAG GAC ACA GCA ATG TAT TAC TGT GCA CGG CAG AAC AAG
TTG AGA GAG GCG CGT CTC CTG TGT CGT TAC ATA ATG ACA CGT GCC GTC TTG TTC
 N   S   L   R   A   E   D   T   A   M   Y   Y   C   A   R   Q   N   K>

390             400             410             420             430
AAA CTG ACC TGG TTT GAC TAC TGG GGA CAG GGG ACC CTT GTG ACA GTC TCC TCT
TTT GAC TGG ACC AAA CTG ATG ACC CCT GTC CCC TGG GAA CAC TGT CAG AGG AGA
 K   L   T   W   F   D   Y   W   G   Q   G   T   L   V   T   V   S   S>

440             450
GCT TCT ACA AAG GGC CCA AGAAA
CGA AGA TGT TTC CCG GGT TCTTT
 A   S   T   K   G   P>
```

Figure 4b)

```
          10         20              30            40            50
GGATGATTCGAAGCCGCCACC ATG AGT GTG CTC ACT CAG GTC CTG GCG TTG CTG CTG
CCTACTAAGCTTCGGCGGTGG TAC TCA CAC GAG TGA GTC CAG GAC CGC AAC GAC GAC
                      M   S   V   L   T   Q   V   L   A   L   L   L>

60             70            80            90           100           110
CTG TGG CTT GCA GGT GCC AGA TGT GAT ATC CAG ATG ACC CAG AGT CCA AGC AGT
GAC ACC GAA CGT CCA CGG TCT ACA CTA TAG GTC TAC TGG GTC TCA GGT TCG TCA
 L   W   L   A   G   A   R   C   D   I   Q   M   T   Q   S   P   S   S>

120           130           140           150           160
CTC TCC GCC AGC GTA GGC GAT CGT GTG ACT ATT ACC TGT CGT ACC AGT GGC AAC
GAG AGG CGG TCG CAT CCG CTA GCA CAC TGA TAA TGG ACA GCA TGG TCA CCG TTG
 L   S   A   S   V   G   D   R   V   T   I   T   C   R   T   S   G   N>

170           180           190           200           210
ATC CAT AAT TAC CTG ACG TGG TAC CAG CAA AAA CTG GGC AAA GCC CCG CAG CTC
TAG GTA TTA ATG GAC TGC ACC ATG GTC GTT TTT GAC CCG TTT CGG GGC GTC GAG
 I   H   N   Y   L   T   W   Y   Q   Q   K   L   G   K   A   P   Q   L>

220           230           240           250           260           270
CTG GTC TAT AAC GCG AAA ACG CTA GCA GAC GGT GTG CCA AGC CGT TTC AGT GGC
GAC CAG ATA TTG CGC TTT TGC GAT CGT CTG CCA CAC GGT TCG GCA AAG TCA CCG
 L   V   Y   N   A   K   T   L   A   D   G   V   P   S   R   F   S   G>

280           290           300           310           320
AGT GGC AGC GGT ACT CAG TTT ACC CTC ACA ATT TCG TCT CTC CAG CCG GAA GAT
TCA CCG TCG CCA TGA GTC AAA TGG GAG TGT TAA AGC AGA GAG GTC GGC CTT CTA
 S   G   S   G   T   Q   F   T   L   T   I   S   S   L   Q   P   E   D>

330           340           350           360           370           380
TTC GCC AAT TAC TAT TGT CAG CAC TTT TGG AGC CTG CCT TTC ACC TTC GGT CAG
AAG CGG TTA ATG ATA ACA GTC GTG AAA ACC TCG GAC GGA AAG TGG AAG CCA GTC
 F   A   N   Y   Y   C   Q   H   F   W   S   L   P   F   T   F   G   Q>

390           400           410
GGC ACT AAA GTA GAA ATC AAA CGT ACG GCGTGC
CCG TGA TTT CAT CTT TAG TTT GCA TGC CGCACG
 G   T   K   V   E   I   K   R   T>
```

Figure 5a)

gH1 End primer T1
GAATAAAAGCTTGCCGCCACC (SEQ ID NO:25)

gH1 End primer B1
TTTCTTGGGCCCTTTGTAGAAG (SEQ ID NO:26)

IC8 gH1 F1
ATGGACTTTGGGCTCAGCTTGATTTTCCTTGTCCTTACTTTAAAAGGTGTGCAG (SEQ ID NO:27)

IC8gH1 F2
TGTGAGGTGCAGCTGGTCGAGTCTGGAGGCGGGCTTGTCCAGCCTGGAGGGAGC (SEQ ID NO:28)

IC8gH1 F3
CTGCGTCTCTCTTGTGCAGCAAGCGGCTTCGACTTTCCCGTTACGATATGTCC (SEQ ID NO:29)

IC8gH1 F4
TGGGTGCGGCAGGCACCTGGGAAGCGCCTGGAGTGGGTGGCATACATTAGCTCC (SEQ ID NO:30)

IC8gH1 F5
GGAGGCGGCTCTACATACTTCCCGGACACCGTCAAGGGCCGTTTCACCATTTCC (SEQ ID NO:31)

IC8 gH1 F6
CGGGACAATGCAAAGAATACCCTTTACCTCCAGATGAACTCTCTCCGCGCAGAG (SEQ ID NO:32)

IC8 gH1 F7
GACACAGCAATGTATTACTGTGCACGGCAGAACAAGAAACTGACCTGGTTTGAC (SEQ ID NO:33)

IC8gH1 F8
TACTGGGGACAGGGGACCCTTGTGACAGTCTCCTCTGCTTCTACAAAGGGCCCAAGAAA (SEQ ID NO:34)

IC8gH1 R1
CAGAGGAGACTGTCACAAGGGTCCCCTGTCCCCAGTAGTCAAACCAGGTCAGTTTCTT (SEQ ID NO:35)

IC8gH1 R2
GTTCTGCCGTGCACAGTAATACATTGCTGTGTCCTCTGCGCGGAGAGAGTTCAT (SEQ ID NO:36)

IC8 gH1 R3
CTGGAGGTAAAGGGTATTCTTTGCATTGTCCCGGGAAATGGTGAAACGGCCCTT (SEQ ID NO:37)

IC8gH1 R4
GACGGTGTCCGGGAAGTATGTAGAGCCGCCTCCGGAGCTAATGTATGCCACCCA (SEQ ID NO:38)

IC8gH1 R5
CTCCAGGCGCTTCCCAGGTGCCTGCCGCACCCAGGACATATCGTAACGGGAAAA (SEQ ID NO:39)

IC8 gH1 R6
GTCGAAGCCGCTTGCTGCACAAGAGAGACGCAGGCTCCCTCCAGGCTGGACAAG (SEQ ID NO:40)

IC8 gH1 R7
CCCGCCTCCAGACTCGACCAGCTGCACCTCACACTGCACACCTTTTAAAGTAAG (SEQ ID NO:41)

IC8 gH1 R8
GACAAGGAAAATCAAGCTGAGCCCAAAGTCCATGGTGGCGGCAAGCTTTTATTC (SEQ ID NO:42)

Figure 5b)

gL1 End primer T1
GGATGATTCGAAGCCGCCAC (SEQ ID NO:43)

gL1 End primer B1
GCACGCCGTACGTTTGATTTC (SEQ ID NO:44)

IC8 gL1 F1
CATGAGTGTGCTCACTCAGGTCCTGGCGTTGCTGCTGCTGTGGCTTGCAGGTGCC (SEQ ID NO:45)

IC8 gL1 F2
AGATGTGATATCCAGATGACCCAGAGTCCAAGCAGTCTCTCCGCCAGCGTAGGCGAT (SEQ ID NO:46)

IC8 gL1 F3
CGTGTGACTATTACCTGTCGTACCAGTGGCAACATCCATAATTACCTGACGTGGTAC (SEQ ID NO:47)

IC8 gL1 F4
CAGCAAAAACTGGGCAAAGCCCCGCAGCTCCTGGTCTATAACGCGAAAACGCTAGCA (SEQ ID NO:48)

IC8 gL1 F5
GACGGTGTGCCAAGCCGTTTCAGTGGCAGTGGCAGCGGTACTCAGTTTACCCTCACA (SEQ ID NO:49)

IC8gL1 F6
ATTTCGTCTCTCCAGCCGGAAGATTTCGCCAATTACTATTGTCAGCACTTTTGGAGC (SEQ ID NO:50)

IC8 gL1 F7
CTGCCTTTCACCTTCGGTCAGGGCACTAAAGTAGAAATCAAACGTACGGCGTGC (SEQ ID NO:51)

IC8gL1 R1
TACTTTAGTGCCCTGACCGAAGGTGAAAGGCAGGCTCCAAAAGTGCTGACAATA (SEQ ID NO:52)

IC8 gL1 R2
GTAATTGGCGAAATCTTCCGGCTGGAGAGACGAAATTGTGAGGGTAAACTGAGTACC (SEQ ID NO:53)

IC8 gL1 R3
GCTGCCACTGCCACTGAAACGGCTTGGCACACCGTCTGCTAGCGTTTTCGCGTTATA (SEQ ID NO:54)

IC8 gL1 R4
GACCAGGAGCTGCGGGGCTTTGCCCAGTTTTTGCTGGTACCACGTCAGGTAATTATG (SEQ ID NO:55)

IC8gL1 R5
GATGTTGCCACTGGTACGACAGGTAATAGTCACACGATCGCCTACGCTGGCGGAGAG (SEQ ID NO:56)

IC8gL1 R6
ACTGCTTGGACTCTGGGTCATCTGGATATCACATCTGGCACCTGCAAGCCACAGCAG (SEQ ID NO:57)

IC8 gL1 R7
CAGCAACGCCAGGACCTGAGTGAGCACACTCATGGTGGCGGCTTCGAATCATCC (SEQ ID NO:58)

Figure 6

```
    CAG CAA AAA CCG GGC AAA GCC CCG CAG CTC CTG GTC TAT AAC GCG AAA ACG
C ATG GTC GTT TTT GGC CCG TTT CGG GGC GTC GAG GAC CAG ATA TTG CGC TTT TGC GAT C
W   Y   Q   Q   K   P   G   K   A   P   Q   L   L   V   Y   N   A   K   T   L   A>
    KpnI                    P                                                      NheI

CAG CAA AAA CCG GGC AAA GCC CCG CAG CTC CTG GTC TAT AAC GCG AAA ACG
C ATG GTC GTT TTT GGC CCG TTT CGG GGC GTC GAG GAC CAG TAG ATA TTG CGC TTT TGC GAT C
W   Y   Q   Q   K   P   G   K   A   P   Q   L   L   Y   I   Y   N   A   K   T   L   A>
    KpnI                    P               G                                      NheI

CCT GGG AAG GGC CTG GAG TGG GTG GCA TAC ATT AGC TCC GGA GGC GGC
GGA CCC TTC CCG GAC CTC ACC CAC CGT ATG TAA TCG AGG CCT CCG CCG
P   G   K   G   L   E   W   V   A   Y   I   S   S   G   G   G>
        K                                           BspEI

GAC ACA GCA GTG TAT TAC TGT GCA CGG CAG AAC AAG AAA CTG ACC TGG TTT GAC
CTG TGT CGT CAC ATA ATG ACA CGT GCC GTC TTG TTC TTT GAC TGG ACC AAA CTG
D   T   A   V   Y   Y   C   A   R   Q   N   K   K   L   T   W   F   D>
        V
```

Figure 11

```
          10        20        30        40        50        60        70
AATTCTCATGTTTGACAGCTTATCATCGACTGCACGGTGCACCAATGCTTCTGGCGTCAGGCAGCCATCG
TTAAGAGTACAAACTGTCGAATAGTAGCTGACGTGCCACGTGGTTACGAAGACCGCAGTCCGTCGGTAGC 80        90       100       110       120       130       140
GAAGCTGTGGTATGGCTGTGCAGGTCGTAAATCACTGCATAATTCGTGTCGCTCAAGGCGCACTCCCGTT
CTTCGACACCATACCGACACGTCCAGCATTTAGTGACGTATTAAGCACAGCGAGTTCCGCGTGAGGGCAA 150       160       170       180       190       200       210
CTGGATAATGTTTTTTGCGCCGACATCATAACGGTTCTGGCAAATATTCTGAAATGAGCTGTTGACAATT
GACCTATTACAAAAAACGCGGCTGTAGTATTGCCAAGACCGTTTATAAGACTTTACTCGACAACTGTTAA 220       230       240       250       260       270       280
AATCATCGGCTCGTATAATGTGTGGAATTGTGAGCGGATAACAATTTCACACAGGAAACAGCGATGAGCT
TTAGTAGCCGAGCATATTACACACCTTAACACTCGCCTATTGTTAAAGTGTGTCCTTTGTCGCTACTCGA 290       300       310       320       330           340
TGGCTGCAGGTCGAGTTCTAGATAACGAGGCGTAAAAA ATG AAA AAG ACA GCT ATC GCA ATT
ACCGACGTCCAGCTCAAGATCTATTGCTCCGCATTTTT TAC TTT TTC TGT CGA TAG CGT TAA
                                        M   K   K   T   A   I   A   I>

350           360           370           380           390
GCA GTG GCC TTG GCT GGT TTC GCT ACC GTA GCG CAA GCT GAT ATC CAG ATG ACC
CGT CAC CGG AAC CGA CCA AAG CGA TGG CAT CGC GTT CGA CTA TAG GTC TAC TGG
 A   V   A   L   A   G   F   A   T   V   A   Q   A   D   I   Q   M   T>

400           410           420           430           440           450
CAG AGT CCA AGC AGT CTC TCC GCC AGC GTA GGC GAT CGT GTG ACT ATT ACC TGT
GTC TCA GGT TCG TCA GAG AGG CGG TCG CAT CCG CTA GCA CAC TGA TAA TGG ACA
 Q   S   P   S   S   L   S   A   S   V   G   D   R   V   T   I   T   C>

460           470           480           490           500
CGT ACC AGT GGC AAC ATC CAT AAT TAC CTG ACG TGG TAC CAG CAA AAA CCG GGC
GCA TGG TCA CCG TTG TAG GTA TTA ATG GAC TGC ACC ATG GTC GTT TTT GGC CCG
 R   T   S   G   N   I   H   N   Y   L   T   W   Y   Q   Q   K   P   G>

510           520           530           540           550
AAA GCC CCG CAG CTC CTG ATC TAT AAC GCG AAA ACG CTA GCA GAC GGT GTG CCA
TTT CGG GGC GTC GAG GAC TAG ATA TTG CGC TTT TGC GAT CGT CTG CCA CAC GGT
 K   A   P   Q   L   L   I   Y   N   A   K   T   L   A   D   G   V   P>

560           570           580           590           600           610
AGC CGT TTC AGT GGC AGT GGC AGC GGT ACT CAG TTT ACC CTC ACA ATT TCG TCT
TCG GCA AAG TCA CCG TCA CCG TCG CCA TGA GTC AAA TGG GAG TGT TAA AGC AGA
 S   R   F   S   G   S   G   S   G   T   Q   F   T   L   T   I   S   S>

620           630           640           650           660
CTC CAG CCG GAA GAT TTC GCC AAT TAC TAT TGT CAG CAC TTT TGG AGC CTG CCT
GAG GTC GGC CTT CTA AAG CGG TTA ATG ATA ACA GTC GTG AAA ACC TCG GAC GGA
 L   Q   P   E   D   F   A   N   Y   Y   C   Q   H   F   W   S   L   P>

670           680           690           700           710           720
TTC ACC TTC GGT CAG GGC ACT AAA GTA GAA ATC AAA CGT ACG GTA GCG GCC CCA
AAG TGG AAG CCA GTC CCG TGA TTT CAT CTT TAG TTT GCA TGC CAT CGC CGG GGT
 F   T   F   G   Q   G   T   K   V   E   I   K   R   T   V   A   A   P>
```

Figure 11b)

```
          730             740             750             760             770
TCT GTC TTC ATC TTC CCG CCA TCT GAT GAG CAG TTG AAA TCT GGA ACT GCC TCT
AGA CAG AAG TAG AAG GGC GGT AGA CTA CTC GTC AAC TTT AGA CCT TGA CGG AGA
 S   V   F   I   F   P   P   S   D   E   Q   L   K   S   G   T   A   S>

780             790             800             810             820
GTT GTG TGC CTG CTG AAT AAC TTC TAT CCC AGA GAG GCC AAA GTA CAG TGG AAG
CAA CAC ACG GAC GAC TTA TTG AAG ATA GGG TCT CTC CGG TTT CAT GTC ACC TTC
 V   V   C   L   L   N   N   F   Y   P   R   E   A   K   V   Q   W   K>

830             840             850             860             870             880
GTG GAT AAC GCC CTC CAA TCG GGT AAC TCC CAG GAG AGT GTC ACA GAG CAG GAC
CAC CTA TTG CGG GAG GTT AGC CCA TTG AGG GTC CTC TCA CAG TGT CTC GTC CTG
 V   D   N   A   L   Q   S   G   N   S   Q   E   S   V   T   E   Q   D>

890             900             910             920             930
AGC AAG GAC AGC ACC TAC AGC CTC AGC AGC ACC CTG ACG CTG AGC AAA GCA GAC
TCG TTC CTG TCG TGG ATG TCG GAG TCG TCG TGG GAC TGC GAC TCG TTT CGT CTG
 S   K   D   S   T   Y   S   L   S   S   T   L   T   L   S   K   A   D>

940             950             960             970             980             990
TAC GAG AAA CAC AAA GTC TAC GCC TGC GAA GTC ACC CAT CAG GGC CTG AGC TCA
ATG CTC TTT GTG TTT CAG ATG CGG ACG CTT CAG TGG GTA GTC CCG GAC TCG AGT
 Y   E   K   H   K   V   Y   A   C   E   V   T   H   Q   G   L   S   S>

1000            1010            1020
CCA GTA ACA AAA AGT TTT AAT AGA GGG GAG TGT TAA
GGT CAT TGT TTT TCA AAA TTA TCT CCC CTC ACA ATT
 P   V   T   K   S   F   N   R   G   E   C   *>

1030            1040            1050            1060            1070
A ATG AAG AAG ACT GCT ATA GCA ATT GCA GTG GCG CTA GCT GGT TTC GCC ACC
T TAC TTC TTC TGA CGA TAT CGT TAA CGT CAC CGC GAT CGA CCA AAG CGG TGG
   M   K   K   T   A   I   A   I   A   V   A   L   A   G   F   A   T>

1080            1090            1100            1110            1120            1130
GTG GCG CAA GCT GAG GTT CAG CTG GTC GAG TCT GGA GGC GGG CTT GTC CAG CCT
CAC CGC GTT CGA CTC CAA GTC GAC CAG CTC AGA CCT CCG CCC GAA CAG GTC GGA
 V   A   Q   A   E   V   Q   L   V   E   S   G   G   G   L   V   Q   P>

1140            1150            1160            1170            1180
GGA GGG AGC CTG CGT CTC TCT TGT GCA GCA AGC GGC TTC GAC TTT TCC CGT TAC
CCT CCC TCG GAC GCA GAG AGA ACA CGT CGT TCG CCG AAG CTG AAA AGG GCA ATG
 G   G   S   L   R   L   S   C   A   A   S   G   F   D   F   S   R   Y>

1190            1200            1210            1220            1230            1240
GAT ATG TCC TGG GTG CGG CAG GCA CCT GGG AAG CGC CTG GAG TGG GTG GCA TAC
CTA TAC AGG ACC CAC GCC GTC CGT GGA CCC TTC GCG GAC CTC ACC CAC CGT ATG
 D   M   S   W   V   R   Q   A   P   G   K   R   L   E   W   V   A   Y>

1250            1260            1270            1280            1290
ATT AGC TCC GGA GGC GGC TCT ACA TAC TTC CCG GAC ACC GTC AAG GGC CGT TTC
TAA TCG AGG CCT CCG CCG AGA TGT ATG AAG GGC CTG TGG CAG TTC CCG GCA AAG
 I   S   S   G   G   G   S   T   Y   F   P   D   T   V   K   G   R   F>

1300            1310            1320            1330            1340
ACC ATT TCC CGG GAC AAT GCA AAG AAT ACC CTT TAC CTC CAG ATG AAC TCT CTC
TGG TAA AGG GCC CTG TTA CGT TTC TTA TGG GAA ATG GAG GTC TAC TTG AGA GAG
 T   I   S   R   D   N   A   K   N   T   L   Y   L   Q   M   N   S   L>
```

Figure 11c)

```
       1350        1360        1370        1380        1390        1400
CGC GCA GAG GAC ACA GCA GTG TAT TAC TGT GCA CGG CAG AAC AAG AAA CTG ACC
GCG CGT CTC CTG TGT CGT CAC ATA ATG ACA CGT GCC GTC TTG TTC TTT GAC TGG
 R   A   E   D   T   A   V   Y   Y   C   A   R   Q   N   K   K   L   T>

1410        1420        1430        1440        1450
TGG TTT GAC TAC TGG GGA CAG GGG ACC CTT GTG ACA GTC TCC TCT GCT TCT ACA
ACC AAA CTG ATG ACC CCT GTC CCC TGG GAA CAC TGT CAG AGG AGA CGA AGA TGT
 W   F   D   Y   W   G   Q   G   T   L   V   T   V   S   S   A   S   T>

1460        1470        1480        1490        1500        1510
AAG GGC CCA TCG GTC TTC CCC CTG GCA CCC TCC TCC AAG AGC ACC TCT GGG GGC
TTC CCG GGT AGC CAG AAG GGG GAC CGT GGG AGG AGG TTC TCG TGG AGA CCC CCG
 K   G   P   S   V   F   P   L   A   P   S   S   K   S   T   S   G   G>

1520        1530        1540        1550        1560
ACA GCG GCC CTG GGC TGC CTG GTC AAG GAC TAC TTC CCC GAA CCG GTG ACG GTG
TGT CGC CGG GAC CCG ACG GAC CAG TTC CTG ATG AAG GGG CTT GGC CAC TGC CAC
 T   A   A   L   G   C   L   V   K   D   Y   F   P   E   P   V   T   V>

1570        1580        1590        1600        1610
TCG TGG AAC TCA GGC GCC CTG ACC AGC GGC GTG CAC ACC TTC CCG GCT GTC CTA
AGC ACC TTG AGT CCG CGG GAC TGG TCG CCG CAC GTG TGG AAG GGC CGA CAG GAT
 S   W   N   S   G   A   L   T   S   G   V   H   T   F   P   A   V   L>

1620        1630        1640        1650        1660        1670
CAG TCC TCA GGA CTC TAC TCC CTC AGC AGC GTG GTG ACC GTG CCC TCC AGC AGC
GTC AGG AGT CCT GAG ATG AGG GAG TCG TCG CAC CAC TGG CAC GGG AGG TCG TCG
 Q   S   S   G   L   Y   S   L   S   S   V   V   T   V   P   S   S   S>

1680        1690        1700        1710        1720
TTG GGC ACC CAG ACC TAC ATC TGC AAC GTG AAT CAC AAG CCC AGC AAC ACC AAG
AAC CCG TGG GTC TGG ATG TAG ACG TTG CAC TTA GTG TTC GGG TCG TTG TGG TTC
 L   G   T   Q   T   Y   I   C   N   V   N   H   K   P   S   N   T   K>

1730        1740        1750        1760        1770        1780
GTC GAC AAG AAA GTT GAG CCC AAA TCT TGT GAC AAA ACT CAC ACA TGC GCC GCG
CAG CTG TTC TTT CAA CTC GGG TTT AGA ACA CTG TTT TGA GTG TGT ACG CGG CGC
 V   D   K   K   V   E   P   K   S   C   D   K   T   H   T   C   A   A>

1790        1800        1810        1820
TGA TGA GGATCCAAGCTTGCGGCCGCGAATTCACTGGCCG
ACT ACT CCTAGGTTCGAACGCCGGCGCTTAAGTGACCGGC
 *   *  >

1830        1840        1850        1860        1870        1880        1890
TCGTTTTACAACGTCGTGACTGGGAAAACCCTGGCGTTACCCAACTTAATCGCCTTGCAGCACATCCCCC
AGCAAAATGTTGCAGCACTGACCCTTTTGGGACCGCAATGGGTTGAATTAGCGGAACGTCGTGTAGGGGG 1900        1910        1920        1930        1940        1950        1960
TTTCGCCAGCTCGCGTAATAGCGAAGAGGCCCGCACCGATCGCCCTTCCCAACAGTTGCGCAGCCTGAAT
AAAGCGGTCGAGCGCATTATCGCTTCTCCGGGCGTGGCTAGCGGGAAGGGTTGTCAACGCGTCGGACTTA 1970        1980        1990        2000        2010        2020        2030
GGCGAATGGCGCCTGATGCGGTATTTTCTCCTTACGCATCTGTGCGGTATTTCACACCGCATAAATTCCC
CCGCTTACCGCGGACTACGCCATAAAAGAGGAATGCGTAGACACGCCATAAAGTGTGGCGTATTTAAGGG 2040        2050
TGTTTTGGCGGATGAGAGAA
ACAAAACCGCCTACTCTCTT
```

METHOD OF TREATING INFLAMMATION BY ADMINISTERING HUMAN IL-1B ANTIBODIES

This application is a divisional application and claims priority under 35 U.S.C. §120 of U.S. patent application Ser. No. 10/544,911, filed Jan. 24, 2006, which claims priority under 35 U.S.C. §371 of International Application No. PCT/GB2004/000463 filed Feb. 6, 2004, which claims priority of United Kingdom application 0303337.0 filed Feb. 13, 2003.

The present invention relates to an antibody molecule having specificity for antigenic determinants of IL-1β. The present invention also relates to the therapeutic uses of the antibody molecule and methods for producing the antibody molecule.

The pro-inflammatory cytokine interleukin-1β (IL-1β) is a member of the IL-1 gene family, which also includes IL-1α and the IL-1 receptor antagonist (IL-IRA) (reviewed by Dinarello, 1996, Blood, 87, 6, 2095-2147). IL-1β is primarily involved in inflammation and has direct effects on endothelial cells and macrophages as well as on both T and B cells. It stimulates bone marrow stromal cells to produce IL-6 as well as a number of colony-stimulating factors and also induces the production of TNFα.

IL-1β is implicated in many pathological conditions that are associated with inflammation. These include infections (viral, bacterial, fungal and parasitic), endotoxic shock, arthritis, rheumatoid arthritis, pelvic inflammatory disease, multiple sclerosis, asthma, osteoarthritis, psoriasis, Alzheimer's Disease, Crohn's disease, Peyronies's disease, heart disease (such as atherosclerosis), colon cancer, coeliac disease, gallbladder disease, Pilonidal disease, peritonitis, meningoencephalitis, other autoimmune disorders, pancreatitis, trauma (surgery), graft-versus host disease and transplant rejection.

IL-1β is also implicated in cancer, osteoporosis and pain signalling.

The involvement of IL-1β in inflammation, pain and other pathological conditions suggests that IL-1β is a good target for drugs and other molecules for the prophylaxis and/or treatment of these conditions.

The mature 17 kDa form of IL-1β exerts its biological effects by binding to the IL-1 receptor IL-1R. Two types of IL-1R exist: the type I receptor IL-1RI and the type II receptor IL-1RII. Binding of IL-1β to IL-1RI leads to recruitment of the receptor accessory protein and signalling. IL-1RII on the other hand, has been termed a 'decoy' receptor, as binding of IL-1β does not transduce a signal. There may be expected to be at least three types of antibody which bind IL-1β:
  (i) antibodies which bind IL-1β but which do not neutralise IL-1RI biological activity (a non-neutralising antibody);
  (ii) antibodies which bind IL-1β and which neutralise IL-1RI biological activity by blocking binding to the IL-1RI; and
  (iii) antibodies which bind IL-1β and which neutralise IL-1RI biological activity but do not block binding to the IL-1RI, such as those antibodies described in US2003/0026806.

Anti IL-1β antibodies have been identified and proposed for use in the treatment of IL-1β mediated diseases and disorders; see for example WO 95/01997.

We have now identified an improved IL-1β antibody that is particularly efficacious in vivo, for example in the in vivo inflammation models described herein. The antibody is a neutralising antibody as defined in alternative (ii), above.

SUMMARY OF THE INVENTION

In a first aspect, the present invention provides a neutralising antibody having specificity for human IL-1β, comprising a heavy chain, wherein the variable domain of the heavy chain comprises at least one of a CDR (complementarity determining region) having the sequence given in SEQ ID NO:5 for CDR-H1, a CDR having the sequence given in SEQ ID NO:6 for CDR-H2 and a CDR having the sequence given in SEQ ID NO:7 for CDR-H3.

The residues in antibody variable domains are conventionally numbered according to a system devised by Kabat et al. This system is set forth in Kabat et al., 1987, in Sequences of Proteins of Immunological Interest, US Department of Health and Human Services, NIH, USA (hereafter "Kabat et al. (supra)"). This numbering system is used in the present specification except where otherwise indicated.

The Kabat residue designations do not always correspond directly with the linear numbering of the amino acid residues. The actual linear amino acid sequence may contain fewer or additional amino acids than in the strict Kabat numbering corresponding to a shortening of, or insertion into, a structural component, whether framework or CDR, of the basic variable domain structure. The correct Kabat numbering of residues may be determined for a given antibody by alignment of residues of homology in the sequence of the antibody with a "standard" Kabat numbered sequence.

The CDRs of the heavy chain variable domain are located at residues 31-35 (CDR-H1), residues 50-65 (CDR-H2) and residues 95-102 (CDR-H3) according to the Kabat numbering system. However, according to Chothia (Chothia, C. and Lesk, A. M. J. Mol. Biol., 196, 901-917 (1987)), the loop equivalent to CDR-H1 extends from residue 26 to residue 32. Thus 'CDR-H1', as used herein, comprises residues 26 to 35, as described by a combination of the Kabat numbering system and Chothia's topological loop definition.

The CDRs of the light chain variable domain are located at residues 24-34 (CDR-L1), residues 50-56 (CDR-L2) and residues 89-97 (CDR-L3) according to the Kabat numbering system. As used herein, the term 'neutralising antibody' describes an antibody that is capable of neutralising the biological signalling activity of IL-1β, in particular by blocking binding of IL-1β to the IL-1RI.

Preferably, an antibody of the first aspect of the present invention comprises a heavy chain wherein at least two of CDR-H1, CDR-H2 and CDR-H3 of the variable domain of the heavy chain are selected from the following: the sequence given in SEQ ID NO:5 for CDR-H1, the sequence given in SEQ ID NO:6 for CDR-H2 and the sequence given in SEQ ID NO:7 for CDR-H3. For example, the antibody may comprise a heavy chain wherein CDR-H1 has the sequence given in SEQ ID NO:5 and CDR-H2 has the sequence given in SEQ ID NO:6. Alternatively, the antibody may comprise a heavy chain wherein CDR-H1 has the sequence given in SEQ ID NO:5 and CDR-H3 has the sequence given in SEQ ID NO:7, or the antibody may comprise a heavy chain wherein CDR-H2 has the sequence given in SEQ ID NO:6 and CDR-H3 has the sequence given in SEQ ID NO:7. For the avoidance of doubt, it is understood that all permutations are included.

More preferably, the antibody of the first aspect of the present invention comprises a heavy chain, wherein the variable domain comprises the sequence given in SEQ ID NO:5 for CDR-H1, the sequence given in SEQ ID NO:6 for CDR-H2 and the sequence given in SEQ ID NO:7 for CDR-H3.

Even more preferably, the antibody of the first aspect of the present invention comprises a heavy chain, wherein the variable domain of the heavy chain comprises the sequence given in SEQ ID NO:3.

Alternatively, the antibody of the first aspect of the present invention comprises a heavy chain, wherein the variable domain of the heavy chain comprises a sequence having at least 60% identity or similarity to the sequence given in SEQ ID NO:3.

"Identity", as used herein, indicates that at any particular position in the aligned sequences, the amino acid residue is identical between the sequences. "Similarity", as used herein, indicates that, at any particular position in the aligned sequences, the amino acid residue is of a similar type between the sequences. For example, leucine may be substituted for isoleucine or valine. Other amino acids which can often be substituted for one another include but are not limited to:

- phenylalanine, tyrosine and tryptophan (amino acids having aromatic side chains);
- lysine, arginine and histidine (amino acids having basic side chains);
- aspartate and glutamate (amino acids having acidic side chains);
- asparagine and glutamine (amino acids having amide side chains); and
- cysteine and methionine (amino acids having sulphur-containing side chains). Degrees of identity and similarity can be readily calculated (Computational Molecular Biology, Lesk, A. M., ed., Oxford University Press, New York, 1988; Biocomputing. Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991). Preferably, the antibody of the first aspect of the present invention comprises a heavy chain, wherein the variable domain of the heavy chain comprises a sequence having at least 90%, 95% or 98% identity or similarity to the sequence given in SEQ ID NO:3.

In a second aspect, the present invention provides a neutralising antibody having specificity for human IL-1β, comprising a light chain, wherein the variable domain of the light chain comprises at least one of a CDR (complementarity determining region) having the sequence given in SEQ ID NO:8 for CDR-L1, a CDR having the sequence given in SEQ ID NO:9 for CDR-L2 and a CDR having the sequence given in SEQ ID NO:10 for CDR-L3.

Preferably, the antibody of the second aspect of the present invention comprises a light chain, wherein at least two of CDR-L1, CDR-L2 and CDR-L3 of the variable domain of the light chain are selected from the following: the sequence given in SEQ ID NO:8 for CDR-L1, the sequence given in SEQ ID NO:9 for CDR-L2 and the sequence given in SEQ ID NO:10 for CDR-L3. For example, the antibody may comprise a light chain wherein CDR-L1 has the sequence given in SEQ ID NO:8 and CDR-L2 has the sequence given in SEQ ID NO:9. Alternatively, the antibody may comprise a light chain wherein CDR-L1 has the sequence given in SEQ ID NO:8 and CDR-L3 has the sequence given in SEQ ID NO:10, or the antibody may comprise a light chain wherein CDR-L2 has the sequence given in SEQ ID NO:9 and CDR-L3 has the sequence given in SEQ ID NO:10. For the avoidance of doubt, it is understood that all permutations are included.

More preferably, the antibody of the second aspect of the present invention comprises a light chain, wherein the variable domain comprises the sequence given in SEQ ID NO:8 for CDR-L1, the sequence given in SEQ ID NO:9 for CDR-L2 and the sequence given in SEQ ID NO:10 for CDR-L3.

Even more preferably, the antibody of the second aspect of the present invention comprises a light chain, wherein the variable domain of the light chain comprises the sequence given in SEQ ID NO:4.

Alternatively, the antibody of the second aspect of the present invention comprises a light chain, wherein the variable domain of the light chain comprises a sequence having at least 60% identity or similarity to the sequence given in SEQ ID NO:4. Preferably, the antibody of the second aspect of the present invention comprises a light chain, wherein the variable domain of the light chain comprises a sequence having at least 90%, 95% or 98% identity or similarity to the sequence given in SEQ ID NO:4.

The antibody molecules of the first and second aspects of the present invention preferably comprise a complementary light chain or a complementary heavy chain, respectively.

Preferably, the antibody according to either of the first and second aspects of the present invention comprises a heavy chain, wherein the variable domain of the heavy chain comprises the sequence given in SEQ ID NO:5 for CDR-H1, the sequence given in SEQ ID NO:6 for CDR-H2 and the sequence given in SEQ ID NO:7 for CDR-H3 and a light chain wherein the variable domain of the light chain comprises the sequence given in SEQ ID NO:8 for CDR-L1, the sequence given in SEQ ID NO:9 for CDR-L2 and the sequence given in SEQ ID NO:10 for CDR-L3.

In a most preferred embodiment of the first and second aspects of the invention, the antibody comprises a heavy chain, wherein the variable domain of the heavy chain comprises the sequence given in SEQ ID NO:3 and a light chain, wherein the variable domain of the light chain comprises the sequence given in SEQ ID NO:4.

In a third aspect of the present invention, there is provided an antibody according to either the first or the second aspect of the invention, wherein said antibody is a monoclonal antibody.

In a preferred embodiment of the third aspect of the invention, the monoclonal antibody comprises a heavy chain, wherein the variable domain of the heavy chain comprises the sequence given in SEQ ID NO:3 and a light chain, wherein the variable domain of the light chain comprises the sequence given in SEQ ID NO:4.

In an alternatively preferred embodiment of the third aspect of the invention, the monoclonal antibody is a murine monoclonal antibody, wherein the monoclonal antibody comprises a heavy chain and a light chain, wherein the variable domain of the heavy chain comprises the sequence given in SEQ ID NO:3, and wherein the variable domain of the light chain comprises the sequence given in SEQ ID NO:4. This murine monoclonal antibody is referred to herein as 'IC8' or as the "donor" antibody or as the "murine monoclonal antibody". The complete nucleotide and amino acid sequences of the variable domains of the heavy and light chains of mouse monoclonal antibody IC8 are shown in FIG. 1 and are given in SEQ ID NOS: 1 to 4. The CDRs given in SEQ ID NOS: 5 to 10 are derived from murine monoclonal antibody IC8.

In a fourth aspect of the invention, there is provided a CDR-grafted antibody molecule, wherein one or more of the CDRs have been obtained from the murine monoclonal antibody IC8. As used herein, the term 'CDR-grafted antibody molecule' refers to an antibody molecule wherein the heavy and/or light chain contains one or more CDRs (including, if desired, one or more modified CDRs) from a donor antibody (e.g. a murine monoclonal antibody) grafted into a heavy and/or light chain variable region framework of an acceptor antibody (e.g. a human antibody). For a review, see Vaughan et al, Nature Biotechnology, 16, 535-539, 1998.

When the CDRs are grafted, any appropriate acceptor variable region framework sequence may be used having regard to the class/type of the donor antibody from which the CDRs are derived, including mouse, primate and human framework regions. Preferably, the CDR-grafted antibody of the fourth aspect of the present invention has a variable domain comprising human acceptor framework regions as well as one or more of the CDRs derived from the donor antibody as referred to above. Thus, provided is a neutralising CDR-grafted antibody wherein the variable domain comprises human acceptor framework regions and non-human donor CDRs.

Examples of human frameworks which can be used in the present invention are KOL, NEWM, REI, EU, TUR, TEI, LAY and POM (Kabat et al., supra). For example, KOL and NEWM can be used for the heavy chain, REI can be used for the light chain and EU, LAY and POM can be used for both the heavy chain and the light chain. Alternatively, human germline sequences may be used.

In a CDR-grafted antibody of the present invention, the acceptor heavy and light chains do not necessarily need to be derived from the same antibody and may, if desired, comprise composite chains having framework regions derived from different chains.

The preferred framework region for the heavy chain of the CDR-grafted antibody of the present invention is derived from the human sub-group VH3 sequence 3-11 (DP-35) shown in FIG. 3 (SEQ ID NO:12) together with JH4. Accordingly, provided is a neutralising CDR-grafted antibody comprising at least one non-human donor CDR wherein the heavy chain framework region is derived from the human subgroup sequence 3-11 (DP-35) together with JH4. The sequence of human JH4 is as follows:
.(YFDY)WGQGTLVTVSS (SEQ ID NO:74). The YFDY motif is part of CDR-H3 and is not part of framework 4 (Ravetch, J V. et al., 1981, Cell, 27, 583-591). The donor sequence is the IC8 VH sequence (SEQ ID NO:11) shown in FIG. 3a.

The preferred framework region for the light chain of the CDR-grafted antibody of the present invention is derived from the human germline sub-group VK1 sequence 012 (DPK9) shown in FIG. 3 (SEQ ID NO:17) together with JK1. Accordingly, provided is a neutralising CDR-grafted antibody comprising at least one non-human donor CDR wherein the light chain framework region is derived from the human subgroup sequence 012 (DPK9) together with JK1. The JK1 sequence is as follows: (WT)FGQGTKVEIK (SEQ ID NO:75). The WT motif is part of CDR-L3 and is not part of framework 4 (Hieter, P A., et al., 1982, J. Biol. Chem., 257, 1516-1522). The donor sequence is the IC8 VL sequence (SEQ ID NO:16) shown in FIG. 3b.

Also, in a CDR-grafted antibody of the present invention, the framework regions need not have exactly the same sequence as those of the acceptor antibody. For instance, unusual residues may be changed to more frequently-occurring residues for that acceptor chain class or type. Alternatively, selected residues in the acceptor framework regions may be changed so that they correspond to the residue found at the same position in the donor antibody (see Reichmann et al. Nature, 332, 323-324, 1988). Such changes should be kept to the minimum necessary to recover the affinity of the donor antibody. A protocol for selecting residues in the acceptor framework regions which may need to be changed is set forth in WO 91/09967.

Preferably, in a CDR-grafted antibody molecule of the present invention, if the acceptor heavy chain has the human DP-35+JH4 sequence, then the acceptor framework regions of the heavy chain comprise, in addition to one or more donor CDRs, a donor residue at position 44 (according to Kabat et al., (supra). The surprising effect on affinity of changing residue 44 to a donor residue was not expected. Thus, in any antibody humanisation process, it will be worth additionally examining the effect of having residue 44 as a donor or acceptor residue. Accordingly, provided is a CDR-grafted antibody, wherein at least the residue at position 44 of the variable domain of the heavy chain is a donor residue.

Alternatively or additionally, if the acceptor heavy chain has the human DP-35+JH4 sequence, then the acceptor framework regions of the heavy chain preferably comprise, in addition to one or more donor CDRs, a donor residue at position 89 (according to Kabat et al., supra). Accordingly, provided is a CDR-grafted antibody, wherein at least the residue at position 44 and/or position 89 of the variable domain of the heavy chain is a donor residue.

Preferably, in a CDR-grafted antibody molecule according to the present invention, if the acceptor light chain has the human sub-group DPK9+JK1 sequence, then the acceptor framework regions of the light chain comprise donor residues at positions 45, 70 and 85 and may additionally comprise donor residues at positions 40 and 48 (according to Kabat et al., supra). Accordingly, provided is a CDR-grafted antibody wherein at least the residue at position 40, 45, 48, 70 and/or 85 is a donor residue. Also provided is a CDR-grafted antibody wherein the residues at positions 45, 70 and 85 are donor residues.

Donor residues are residues from the donor antibody, i.e. the antibody from which the CDRs were originally derived, which in the case of the present invention is the murine monoclonal antibody IC8.

In an alternative embodiment of the first or fourth aspects of the present invention, the heavy chain preferably comprises the sequence of gH1 (SEQ ID NO:13), gH2 (SEQ ID NO:14) or gH3 (SEQ ID NO:15). The sequences of the variable domains of these grafted heavy chains are shown in FIG. 3a.

In an alternative embodiment of the second or fourth aspects of the present invention, the light chain preferably comprises the sequence of gL1 (SEQ ID NO:18), gL2 (SEQ ID NO:19) or gL3 (SEQ ID NO:20). The sequences of the variable domains of these grafted light chains are shown in FIG. 3b.

More preferably, an antibody molecule according to the alternative embodiment of the second or fourth aspects of the present invention comprises a heavy chain comprising the sequence of gH1 (SEQ ID NO:13), gH2 (SEQ ID NO:14) or gH3 (SEQ ID NO:15) and a light chain comprising the sequence of gL1 (SEQ ID NO:18), gL2 (SEQ ID NO:19) or gL3 (SEQ ID NO:20).

Even more preferably, the heavy chain of the antibody molecule according to the alternative embodiment of the second or fourth aspects of the present invention comprises variable domain gH3 (SEQ ID NO:15) and the light chain of the antibody molecule of the present invention comprises variable domain gL3 (SEQ ID NO:20).

In a fifth aspect of the invention, there is provided an antibody according to any one of the first to fourth aspects of the present invention, which binds to the same epitope as IC8. Alternatively, there is provided a neutralising antibody having specificity for human IL-1β, which binds to the same epitope as an antibody whose heavy chain comprises the sequence gH3 (SEQ ID NO:15) and whose light chain comprises the sequence gL3 (SEQ ID NO:20).

The antibody molecule of the present invention may comprise a complete antibody molecule having full length heavy and light chains or a fragment thereof, such as a Fab, modified Fab, Fab', F(ab')$_2$, Fv or scFv fragment. Alternatively, it may comprise a light chain or heavy chain monomer or dimer or a single chain antibody, e.g. a single chain Fv in which the heavy and light chain variable domains are joined by a peptide linker. Similarly, the heavy and light chain variable regions may be combined with other antibody domains as appropriate.

The antibody molecule of the present invention may have an effector or a reporter molecule attached to it. For instance, it may have a macrocycle for chelating a heavy metal atom, or a toxin, such as ricin, attached to it by a covalent bridging structure.

Preferably, the antibody of the present invention may be modified to enable an effector or reporter molecule to be attached to it. Most preferably, the antibody molecule of the present invention is a modified Fab fragment as described below.

Alternatively, procedures of recombinant DNA technology may be used to produce an antibody molecule in which the Fc fragment (CH2, CH3 and hinge domains), the CH2 and CH3 domains or the CH3 domain of a complete immunoglobulin molecule has (have) been replaced by, or has (have) attached thereto by peptide linkage, a functional non-immunoglobulin protein, such as an enzyme or toxin molecule. Alternatively, it is preferred that the antibody molecule of the present invention is a modified Fab fragment wherein the modification is the addition to the C-terminal end of its heavy chain one or more amino acids to allow the attachment of an effector or reporter molecule. Preferably, the additional amino acids form a modified hinge region containing one or two cysteine residues to which the effector or reporter molecule may be attached.

Also provided is a neutralising antibody molecule according to the present invention having an effector or a reporter molecule attached to it. Effector or reporter molecules include a molecule such as a cytotoxic agent, a radionuclide or drug moiety. Other molecules which may be attached include a toxin such as abrin, ricin A, pseudomonas exotoxin, or diphtheria toxin, a protein such as tumour necrosis factor, α-interferon, β-interferon, nerve growth factor, platelet derived growth factor or tissue plasminogen activator, a thrombotic agent or an anti-angiogenic agent, e.g. angiostatin or endostatin, or, a biological response modifier such as a lymphokine, interleukin-1 (IL-1), interleukin-2 (IL-2), interleukin-6 (IL-6), granulocyte macrophage colony stimulating factor (GM-CSF), granulocyte colony stimulating factor (G-CSF), nerve growth factor (NGF) or other growth factor.

A preferred effector group is a polymer molecule, which may be attached to the modified Fab fragment to increase its half-life in vivo.

The polymer molecule may, in general, be a synthetic or a naturally occurring polymer, for example an optionally substituted straight or branched chain polyalkylene, polyalkenylene or polyoxyalkylene polymer or a branched or unbranched polysaccharide, e.g. a homo- or hetero-polysaccharide.

Particular optional substituents which may be present on the above-mentioned synthetic polymers include one or more hydroxy, methyl or methoxy groups.

Particular examples of synthetic polymers include optionally substituted straight or branched chain poly(ethyleneglycol), poly(propyleneglycol) poly(vinylalcohol) or derivatives thereof, especially optionally substituted poly(ethyleneglycol) such as methoxypoly(ethyleneglycol) or derivatives thereof.

Particular naturally occurring polymers include lactose, amylose, dextran, glycogen or derivatives thereof.

"Derivatives" as used herein is intended to include reactive derivatives, for example thiol-selective reactive groups such as maleimides and the like. The reactive group may be linked directly or through a linker segment to the polymer. It will be appreciated that the residue of such a group will in some instances form part of the product as the linking group between the antibody fragment and the polymer.

The size of the polymer may be varied as desired, but will generally be in an average molecular weight range from 500 Da to 50000 Da, preferably from 5000 to 40000 Da and more preferably from 25000 to 40000 Da. The polymer size may in particular be selected on the basis of the intended use of the product. Thus, for example, where the product is intended to leave the circulation and penetrate tissue, for example for use in the treatment of a tumour, it may be advantageous to use a small molecular weight polymer, for example with a molecular weight of around 5000 Da. For applications where the product remains in the circulation, it may be advantageous to use a higher molecular weight polymer, for example having a molecular weight in the range from 25000 Da to 40000 Da.

Particularly preferred polymers include a polyalkylene polymer, such as a poly(ethyleneglycol) or, especially, a methoxypoly(ethyleneglycol) or a derivative thereof, and especially with a molecular weight in the range from about 25000 Da to about 40000 Da.

Each polymer molecule attached to the modified antibody fragment may be covalently linked to the sulphur atom of a cysteine residue located in the fragment. The covalent linkage will generally be a disulphide bond or, in particular, a sulphur-carbon bond.

Where desired, the antibody fragment may have one or more effector or reporter molecules attached to it. The effector or reporter molecules may be attached to the antibody fragment through any available amino acid side-chain or terminal amino acid functional group located in the fragment, for example any free amino, imino, hydroxyl or carboxyl group.

An activated polymer may be used as the starting material in the preparation of polymer-modified antibody fragments as described above. The activated polymer may be any polymer containing a thiol reactive group such as an α-halocarboxylic acid or ester, e.g. iodoacetamide, an imide, e.g. maleimide, a vinyl sulphone or a disulphide. Such starting materials may be obtained commercially (for example from Nektar, formerly Shearwater Polymers Inc., Huntsville, Ala., USA) or may be prepared from commercially available starting materials using conventional chemical procedures. Particular PEG molecules include 20K methoxy-PEG-amine (obtainable from Nektar, formerly Shearwater; Rapp Polymere; and Sun-Bio) and M-PEG-SPA (obtainable from Nektar, formerly Shearwater).

As regards attaching poly(ethyleneglycol) (PEG) moieties, reference is made to "Poly(ethyleneglycol) Chemistry, Biotechnical and Biomedical Applications", 1992, J. Milton Harris (ed), Plenum Press, New York; "Poly(ethyleneglycol) Chemistry and Biological Applications", 1997, J. Milton Harris and S. Zalipsky (eds), American Chemical Society, Washington D.C. and "Bioconjugation Protein Coupling Techniques for the Biomedical Sciences", 1998, M. Aslam and A. Dent, Grove Publishers, New York.

Where it is desired to obtain an antibody fragment linked to an effector or reporter molecule, this may be prepared by standard chemical or recombinant DNA procedures in which the antibody fragment is linked either directly or via a coupling agent to the effector or reporter molecule either before or after reaction with the activated polymer as appropriate. Particular chemical procedures include, for example, those described in WO 93/06231, WO 92/22583, WO 89/00195 and WO 89/01476. Alternatively, where the effector or reporter molecule is a protein or polypeptide the linkage may be achieved using recombinant DNA procedures, for example as described in WO 86/01533 and EP0392745.

Preferably, the modified Fab fragment of the present invention is PEGylated (i.e. has PEG (poly(ethyleneglycol)) covalently attached thereto) according to the method disclosed in EP-A-0948544. Preferably the antibody molecule of the present invention is a PEGylated modified Fab fragment as shown in FIG. 12. The modified Fab fragment preferably has a maleimide group covalently linked to a single thiol group in a modified hinge region. A lysine residue is preferably covalently linked to the maleimide group. To each of the amine groups on the lysine residue is preferably attached a methoxypoly(ethyleneglycol) polymer having a molecular weight of approximately 20,000 Da. The total molecular weight of the entire effector molecule is therefore approximately 40,000 Da. Accordingly, provided is a neutralising antibody having attached to one of the cysteine residues at the C-terminal end of the heavy chain a lysyl-maleimide or lysyl bis-maleimide group wherein each amino group of the lysyl residue has covalently linked to it a methoxypoly(ethyleneglycol) residue having a molecular weight of about 20,000 Da. For example, the molecular weight may be 15,000-25,000 Da, or preferably 18,000-22,000 Da, and even more preferably 19,000-21,000 Da.

In a preferred embodiment, the present invention provides a neutralising antibody molecule having specificity for human IL-1β, which is a modified Fab fragment having a heavy chain comprising the sequence given in SEQ ID NO:15 and a light chain comprising the sequence given in SEQ ID NO:20 and having at the C-terminal end of its heavy chain a modified hinge region containing one cysteine residue to which an effector or reporter molecule may be attached.

In another preferred embodiment, provided is a neutralising antibody molecule having specificity for human IL-1β, which is a modified Fab fragment having a heavy chain comprising the sequence given in SEQ ID NO:15 and a light chain comprising the sequence given in SEQ ID NO:20 and having at the C-terminal end of its heavy chain a modified hinge region containing one cysteine residue to which an effector or reporter molecule is attached.

More preferably, provided is a neutralising antibody molecule having specificity for human IL-1β, which is a modified Fab fragment having a heavy chain comprising the sequence given in SEQ ID NO:15 and a light chain comprising the sequence given in SEQ ID NO:20 having attached to the cysteine residue at the C-terminal end of the heavy chain a lysyl-maleimide group, wherein each amino group of the lysyl residue has covalently linked to it a methoxypoly(ethyleneglycol) residue having a molecular weight of about 20,000 Da.

Even more preferably, provided is a neutralising antibody molecule, wherein its heavy chain comprises or consists of amino acid residue numbers 22 to 251 of the sequence given in SEQ ID NO:71, and wherein its light chain comprises or consists of amino acid residue numbers 22 to 235 of the sequence given in SEQ ID NO:70. Amino acid residue numbers 1 to 21 of the sequences given in SEQ ID NOS: 70 and 71 represent the *E. Coli* leader sequence which is most preferably cleaved to give a neutralising antibody molecule of the present invention.

Most preferably, provided is a neutralising antibody molecule, wherein its heavy chain comprises or consists of amino acid residue numbers 22 to 251 of the sequence given in SEQ ID NO:71, and wherein its light chain comprises or consists of amino acid residue numbers 22 to 235 of the sequence given in SEQ ID NO:70 having attached to the cysteine residue at the C-terminal end of the heavy chain a lysyl-maleimide group, wherein each amino group of the lysyl residue has covalently linked to it a methoxypoly(ethyleneglycol) residue having a molecular weight of about 20,000 Da.

Also provided is a neutralising antibody molecule having specificity for human IL-1β, which binds to the same epitope as a neutralising antibody which comprises a light chain comprising the sequence given in SEQ ID NO:20.

The constant region domains of the antibody molecule of the present invention, if present, may be selected having regard to the proposed function of the antibody molecule, and in particular the effector functions which may be required. For example, the constant region domains may be human IgA, IgD, IgE, IgG or IgM domains. In particular, human IgG constant region domains may be used, especially of the IgG1 and IgG3 isotypes when the antibody molecule is intended for therapeutic uses and antibody effector functions are required. Alternatively, IgG2 and IgG4 isotypes may be used when the antibody molecule is intended for therapeutic purposes and antibody effector functions are not required, e.g. for simply blocking IL-1β activity.

The antibody molecule of the present invention preferably has a binding affinity of at least $4.4 \times 10^{-10}$ M, more preferably at least $3.2 \times 10^{-10}$ M.

The present invention also relates to variants of the antibody molecules of the present invention, which have an improved affinity for IL-1β. Such variants can be obtained by a number of affinity maturation protocols including mutating the CDRs (Yang et al., J. Mol. Biol., 254, 392-403, 1995), chain shuffling (Marks et al., Bio/Technology, 10, 779-783, 1992), use of mutator strains of *E. coli* (Low et al., J. Mol. Biol., 250, 359-368, 1996), DNA shuffling (Patten et al., Curr. Opin. Biotechnol., 8, 724-733, 1997), phage display (Thompson et al., J. Mol. Biol., 256, 77-88, 1996) and sexual PCR (Crameri et al., Nature, 391, 288-291, 1998). Vaughan et al. (supra) discusses these methods of affinity maturation.

The present invention also provides an isolated DNA sequence encoding the heavy and/or light chain(s) of the antibody molecule of the present invention. Preferably, the DNA sequence encodes the heavy or the light chain of the antibody molecule of the present invention. The DNA sequence of the present invention may comprise synthetic DNA, for instance produced by chemical processing, cDNA, genomic DNA or any combination thereof.

DNA sequences which encode the antibody molecule of the present invention can be obtained by methods well known to those skilled in the art. For example, DNA sequences coding for part or all of the antibody heavy and light chains may be synthesised as desired from the determined DNA sequences or on the basis of the corresponding amino acid sequences.

DNA coding for acceptor framework sequences is widely available to those skilled in the art and can be readily synthesised on the basis of their known amino acid sequences.

Standard techniques of molecular biology may be used to prepare DNA sequences coding for the antibody molecule of the present invention. Desired DNA sequences may be synthesised completely or in part using oligonucleotide synthesis techniques. Site-directed mutagenesis and polymerase chain reaction (PCR) techniques may be used as appropriate.

The present invention also relates to a cloning or expression vector comprising one or more DNA sequences of the present invention. Accordingly, provided is a cloning or expression vector comprising one or more DNA sequences encoding an antibody of the present invention. Preferably, the cloning or expression vector comprises two DNA sequences, encoding the light chain and the heavy chain of the antibody molecule of the present invention, respectively. Preferably, a vector according to the present invention comprises the sequence given in SEQ ID NO:69.

General methods by which the vectors may be constructed, transfection methods and culture methods are well known to those skilled in the art. In this respect, reference is made to "Current Protocols in Molecular Biology", 1999, F. M. Ausubel (ed), Wiley Interscience, New York and the Maniatis Manual produced by Cold Spring Harbor Publishing.

Also provided is a host cell comprising one or more cloning or expression vectors comprising one or more DNA sequences encoding an antibody of the present invention. Any suitable host cell/vector system may be used for expression of the DNA sequences encoding the antibody molecule of the present invention. Bacterial, for example $E.\ coli$, and other microbial systems may be used or eukaryotic, for example mammalian, host cell expression systems may also be used. Suitable mammalian host cells include CHO, myeloma or hybridoma cells.

The present invention also provides a process for the production of an antibody molecule according to the present invention comprising culturing a host cell containing a vector of the present invention under conditions suitable for leading to expression of protein from DNA encoding the antibody molecule of the present invention, and isolating the antibody molecule.

The antibody molecule may comprise only a heavy or light chain polypeptide, in which case only a heavy chain or light chain polypeptide coding sequence needs to be used to transfect the host cells. For production of products comprising both heavy and light chains, the cell line may be transfected with two vectors, a first vector encoding a light chain polypeptide and a second vector encoding a heavy chain polypeptide. Alternatively, a single vector may be used, the vector including sequences encoding light chain and heavy chain polypeptides.

As the antibodies of the present invention are useful in the treatment and/or prophylaxis of a pathological condition, the present invention also provides a pharmaceutical or diagnostic composition comprising an antibody molecule of the present invention in combination with one or more of a pharmaceutically acceptable excipient, diluent or carrier. Accordingly, provided is the use of an antibody of the invention for the manufacture of a medicament. The composition will usually be supplied as part of a sterile, pharmaceutical composition that will normally include a pharmaceutically acceptable carrier. A pharmaceutical composition of the present invention may additionally comprise a pharmaceutically-acceptable adjuvant.

The present invention also provides a process for preparation of a pharmaceutical or diagnostic composition comprising adding and mixing the antibody molecule of the present invention together with one or more of a pharmaceutically acceptable excipient, diluent or carrier.

The antibody molecule may be the sole active ingredient in the pharmaceutical or diagnostic composition or may be accompanied by other active ingredients including other antibody ingredients, for example anti-T cell, anti-IFNγ or anti-LPS antibodies, or non-antibody ingredients such as xanthines.

The pharmaceutical compositions preferably comprise a therapeutically effective amount of the antibody of the invention. The term "therapeutically effective amount" as used herein refers to an amount of a therapeutic agent needed to treat, ameliorate or prevent a targeted disease or condition, or to exhibit a detectable therapeutic or preventative effect. For any antibody, the therapeutically effective amount can be estimated initially either in cell culture assays or in animal models, usually in rodents, rabbits, dogs, pigs or primates. The animal model may also be used to determine the appropriate concentration range and route of administration. Such information can then be used to determine useful doses and routes for administration in humans.

The precise therapeutically effective amount for a human subject will depend upon the severity of the disease state, the general health of the subject, the age, weight and gender of the subject, diet, time and frequency of administration, drug combination(s), reaction sensitivities and tolerance/response to therapy. This amount can be determined by routine experimentation and is within the judgement of the clinician. Generally, a therapeutically effective amount will be from 0.01 mg/kg to 50 mg/kg, preferably 0.1 mg/kg to 20 mg/kg. Pharmaceutical compositions may be conveniently presented in unit dose forms containing a predetermined amount of an active agent of the invention per dose.

Compositions may be administered individually to a patient or may be administered in combination (e.g. simultaneously, sequentially or separately) with other agents, drugs or hormones.

The dose at which the antibody molecule of the present invention is administered depends on the nature of the condition to be treated, the extent of the inflammation present and on whether the antibody molecule is being used prophylactically or to treat an existing condition.

The frequency of dose will depend on the half-life of the antibody molecule and the duration of its effect. If the antibody molecule has a short half-life (e.g. 2 to 10 hours) it may be necessary to give one or more doses per day. Alternatively, if the antibody molecule has a long half life (e.g. 2 to 15 days) it may only be necessary to give a dosage once per day, once per week or even once every 1 or 2 months.

The pharmaceutically acceptable carrier should not itself induce the production of antibodies harmful to the individual receiving the composition and should not be toxic. Suitable carriers may be large, slowly metabolised macromolecules such as proteins, polypeptides, liposomes, polysaccharides, polylactic acids, polyglycolic acids, polymeric amino acids, amino acid copolymers and inactive virus particles.

Pharmaceutically acceptable salts can be used, for example mineral acid salts, such as hydrochlorides, hydrobromides, phosphates and sulphates, or salts of organic acids, such as acetates, propionates, malonates and benzoates.

Pharmaceutically acceptable carriers in therapeutic compositions may additionally contain liquids such as water, saline, glycerol and ethanol. Additionally, auxiliary substances, such as wetting or emulsifying agents or pH buffering substances, may be present in such compositions. Such carriers enable the pharmaceutical compositions to be formulated as tablets, pills, dragees, capsules, liquids, gels, syrups, slurries and suspensions, for ingestion by the patient.

Preferred forms for administration include forms suitable for parenteral administration, e.g. by injection or infusion, for example by bolus injection or continuous infusion. Where the product is for injection or infusion, it may take the form of a suspension, solution or emulsion in an oily or aqueous vehicle and it may contain formulatory agents, such as suspending, preservative, stabilising and/or dispersing agents. Alternatively, the antibody molecule may be in dry form, for reconstitution before use with an appropriate sterile liquid.

Once formulated, the compositions of the invention can be administered directly to the subject. The subjects to be treated can be animals. However, it is preferred that the compositions are adapted for administration to human subjects.

The pharmaceutical compositions of this invention may be administered by any number of routes including, but not limited to, oral, intravenous, intramuscular, intra-arterial, intramedullary, intrathecal, intraventricular, transdermal, transcutaneous (for example, see WO 98/20734), subcutaneous, intraperitoneal, intranasal, enteral, topical, sublingual, intravaginal or rectal routes. Hyposprays may also be used to administer the pharmaceutical compositions of the invention. Typically, the therapeutic compositions may be prepared as injectables, either as liquid solutions or suspensions. Solid forms suitable for solution in, or suspension in, liquid vehicles prior to injection may also be prepared.

Direct delivery of the compositions will generally be accomplished by injection, subcutaneously, intraperitoneally, intravenously or intramuscularly, or delivered to the interstitial space of a tissue. The compositions can also be administered into a lesion. Dosage treatment may be a single dose schedule or a multiple dose schedule.

It will be appreciated that the active ingredient in the composition will be an antibody molecule. As such, it will be susceptible to degradation in the gastrointestinal tract. Thus, if the composition is to be administered by a route using the gastrointestinal tract, the composition will need to contain agents which protect the antibody from degradation but which release the antibody once it has been absorbed from the gastrointestinal tract.

A thorough discussion of pharmaceutically acceptable carriers is available in Remington's Pharmaceutical Sciences (Mack Publishing Company, N.J. 1991).

It is also envisaged that the antibody of the present invention will be administered by use of gene therapy. In order to achieve this, DNA sequences encoding the heavy and light chains of the antibody molecule under the control of appropriate DNA components are introduced into a patient such that the antibody chains are expressed from the DNA sequences and assembled in situ.

The present invention also provides an antibody molecule for use in the control of inflammation. Preferably, the antibody molecule can be used to reduce the inflammatory process or to prevent the inflammatory process.

The present invention also provides the antibody molecule of the present invention for use in the treatment or prophylaxis of a pathological disorder that is mediated by IL-1β or associated with an increased level of IL-1β. Preferably, the pathological condition is selected from the group consisting of infections (viral, bacterial, fungal and parasitic), endotoxic shock associated with infection, arthritis, rheumatoid arthritis, pelvic inflammatory disease, Alzheimer's Disease, Crohn's disease, Peyronie's Disease, coeliac disease, gallbladder disease, Pilonidal disease, peritonitis, meningoencephalitis, other autoimmune disorders, pancreatitis, trauma (surgery), graft-versus-host disease, transplant rejection, cancer (both solid tumours such as melanomas, hepatoblastomas, sarcomas, squamous cell carcinomas, transitional cell cancers, ovarian cancers and hematologic malignancies and in particular acute myelogenous leukaemia, chronic myelogenous leukemia, gastric cancer and colon cancer), heart disease including ischaemic diseases such as myocardial infarction as well as atherosclerosis, intravascular coagulation, bone resorption, osteoporosis, periodontitis and hypochlorhydia.

The present invention also provides an antibody molecule according to the present invention for use in the treatment or prophylaxis of pain.

The present invention further provides the use of an antibody molecule according to the present invention in the manufacture of a medicament for the treatment or prophylaxis of a pathological disorder that is mediated by IL-1β or associated with an increased level of IL-1β.

The present invention further provides the use of an antibody molecule according to the present invention in the manufacture of a medicament for the treatment or prophylaxis of pain.

An antibody molecule of the present invention may be utilised in any therapy where it is desired to reduce the effects of IL-1β in the human or animal body. IL-1β may be circulating in the body of may be present in an undesirably high level localised at a particular site in the body, for example a site of inflammation.

The antibody molecule of the present invention is preferably used for the control of inflammation.

The present invention also provides a method of treating human or animal subjects suffering from or at risk of a disorder mediated by IL-1β, the method comprising administering to the subject an effective amount of the antibody molecule of the present invention.

The antibody molecule of the present invention may also be used in diagnosis, for example in the in vivo diagnosis and imaging of disease states involving IL-1β.

The present invention is further described by way of illustration only in the following examples, which refer to the accompanying Figures, in which:

FIG. 1a) shows the nucleotide and amino acid sequence (SEQ ID NOS:1 and 3, respectively) of the variable domains of the heavy chain, and FIG. 1b) shows the nucleotide and amino acid sequence (SEQ ID NOS:2 and 4, respectively) of the variable domains of the light chain of murine monoclonal antibody IC8.

FIG. 2 shows the vectors MRR14 and pMRR10.

FIG. 3 shows the graft design for the IC8 heavy (FIG. 3a; SEQ ID NOS:11-15) and light chain (FIG. 3b; SEQ ID NOS: 16-20) sequences. The symbol (|) highlights differences between donor:acceptor:grafted framework sequences. CDR's are single underlined for the IC8 sequences. These are as defined by Kabat, except for CDR-H1 which encompasses both Kabat and Chothia definitions. Double-underlined sequences are donor residues retained in the grafts. Starred (*) residues are common in human sub-group VH3 germline sequences, but not present in this particular germline—these are not considered mouse residues even though they are present in the original donor sequence.

FIG. 4 shows the nucleotide and amino acid sequences of the designed genes gH1 (FIG. 4a) and gL1 (FIG. 4b).

FIG. 5 shows the oligonucleotides that were used for gene construction.

FIG. 6 shows the oligonucleotide cassettes that were used for further grafts. Shown are: the IC8gL2 sense strand sequence (SEQ ID NO:59), the reverse strand sequence (SEQ ID NO:72) and the corresponding amino acid sequence (SEQ ID NO:60); the IC8gL3 sense strand sequence (SEQ ID NO:61), the reverse strand sequence (SEQ ID NO:73) and the corresponding amino acid sequence (SEQ ID NO:62); the IC8gH2 sense strand sequence (SEQ ID NO:63), the reverse strand sequence (SEQ ID NO:64) and the corresponding amino acid sequence (SEQ ID NO:65), and the IC8gH3 sense strand sequence (SEQ ID NO:66), the reverse strand sequence (SEQ ID NO:67) and the corresponding amino acid sequence (SEQ ID NO:68). Underlined residues denote changed amino acids.

Figure 7:
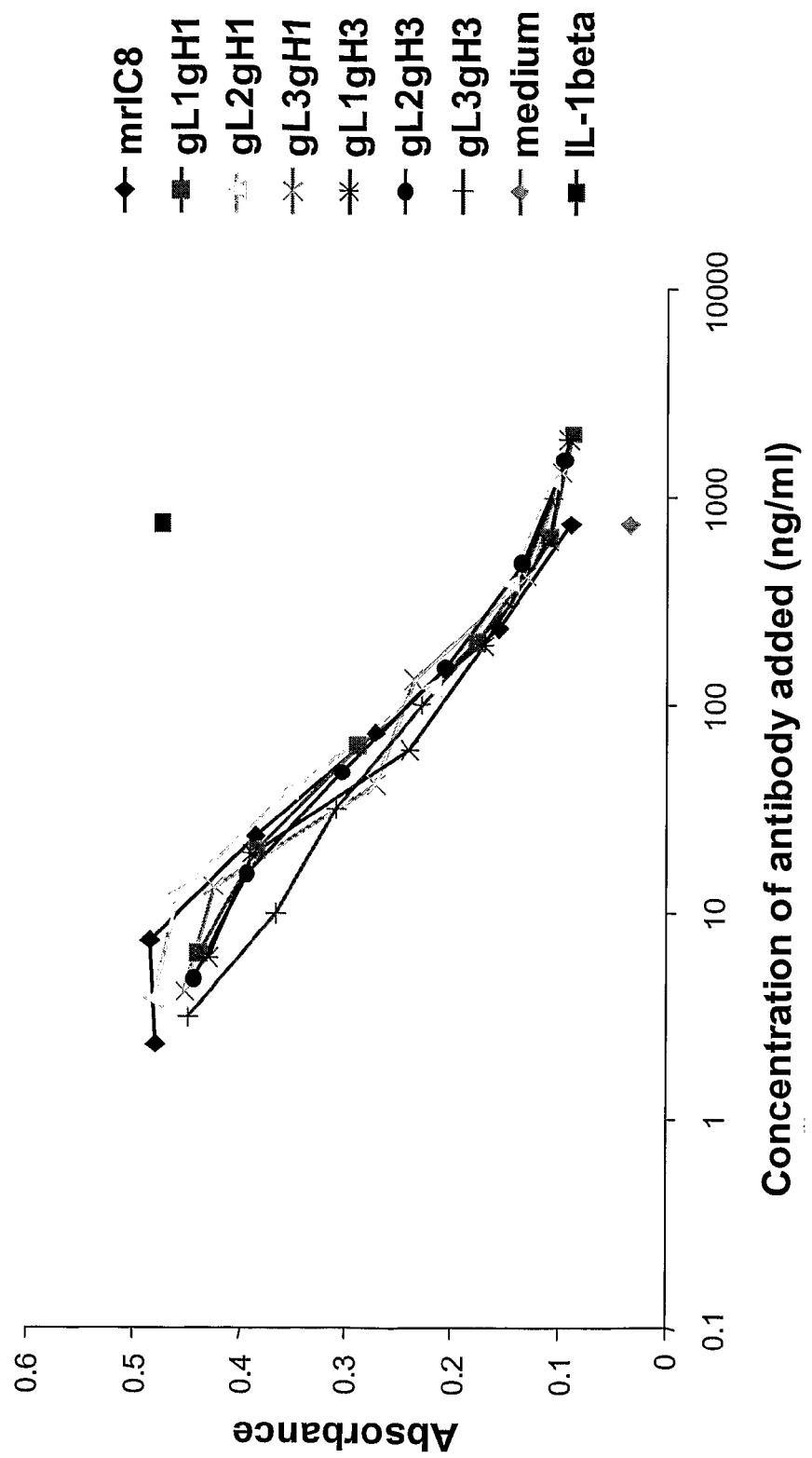

FIG. 7 shows the results from the IL-1β neutralisation assay with IC8 grafts.

Figure 8:
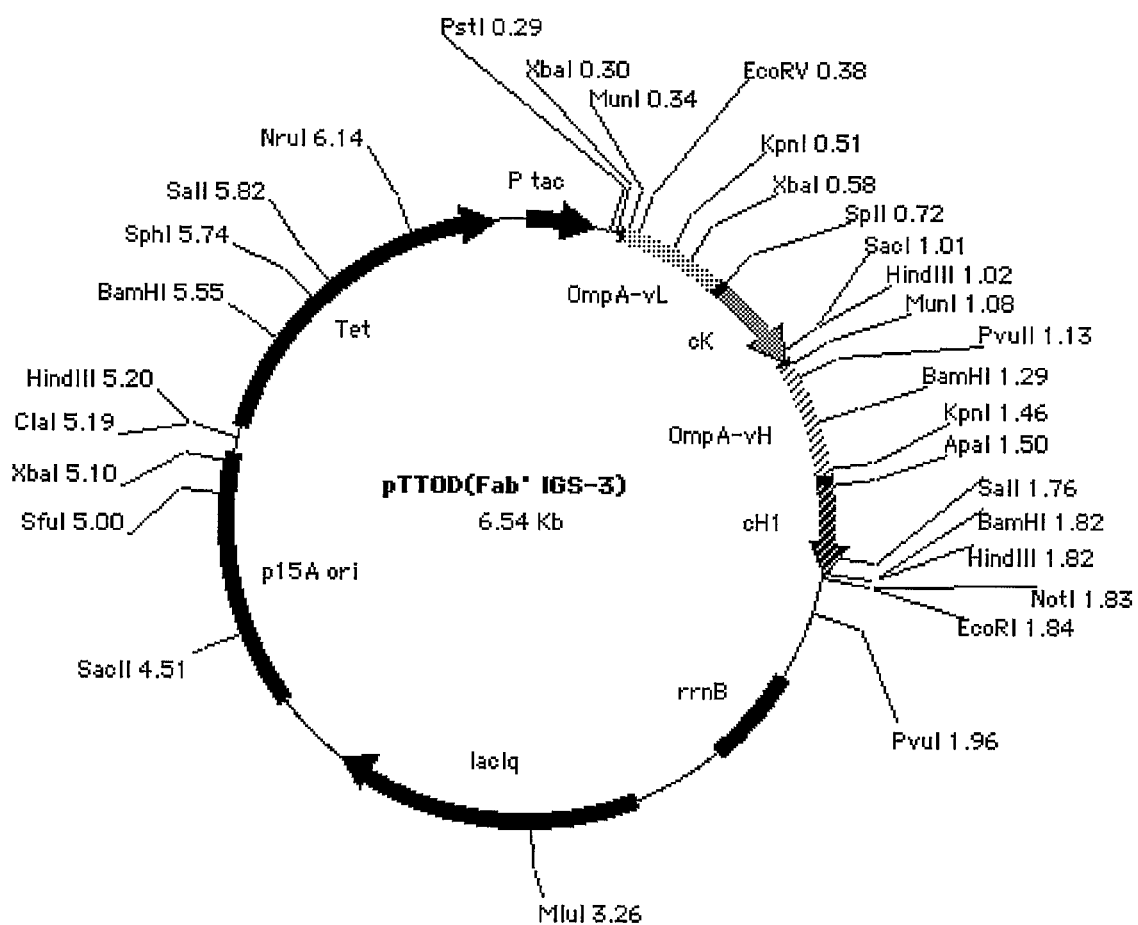

FIG. 8 shows a map of the vector pTTOD(Fab').

Figure 9:
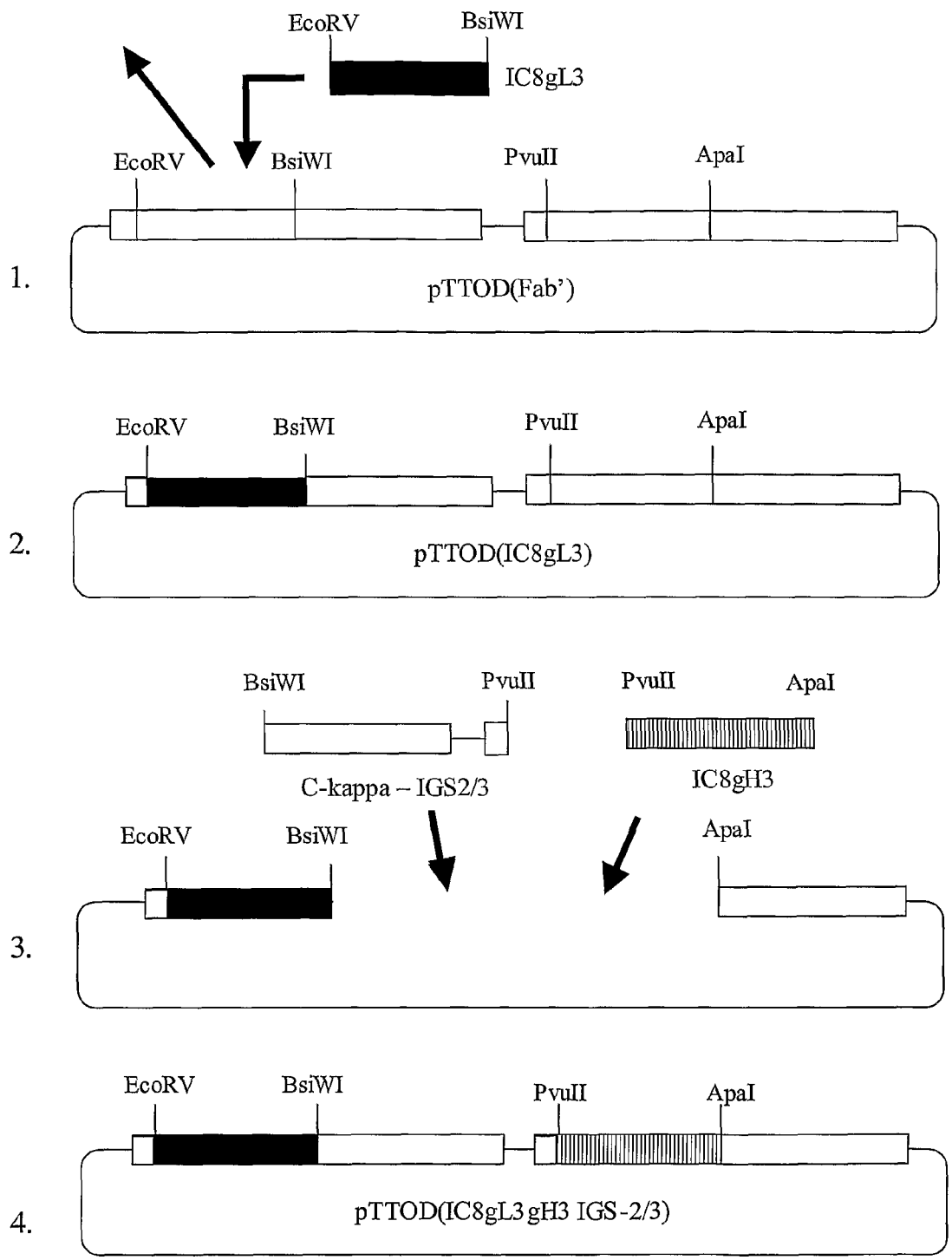

FIG. 9 shows steps 1-4 in the cloning of IC8 V-region genes into the intermediate vector pTTOD(Fab').

Figure 10:
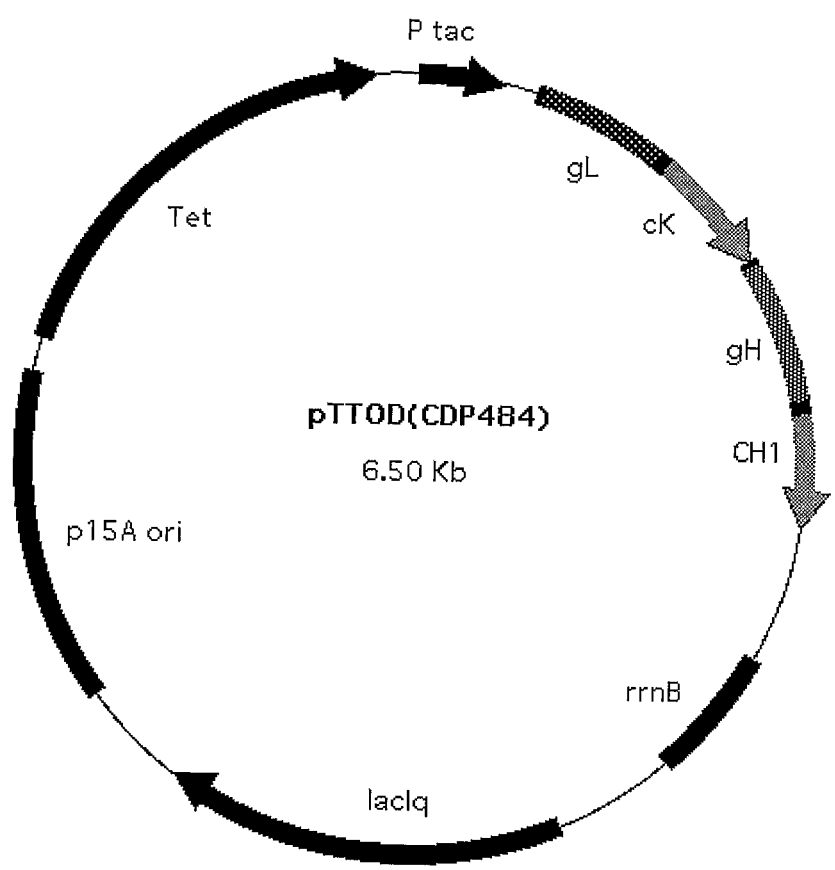

FIG. 10 shows a map of vector pTTOD(gH3gL3 Fab' IGS-2).

FIG. 11 shows the coding and flanking sequence of pTTOD (gH3gL3 Fab' IGS-2); SEQ ID NO:69.

Figure 12:
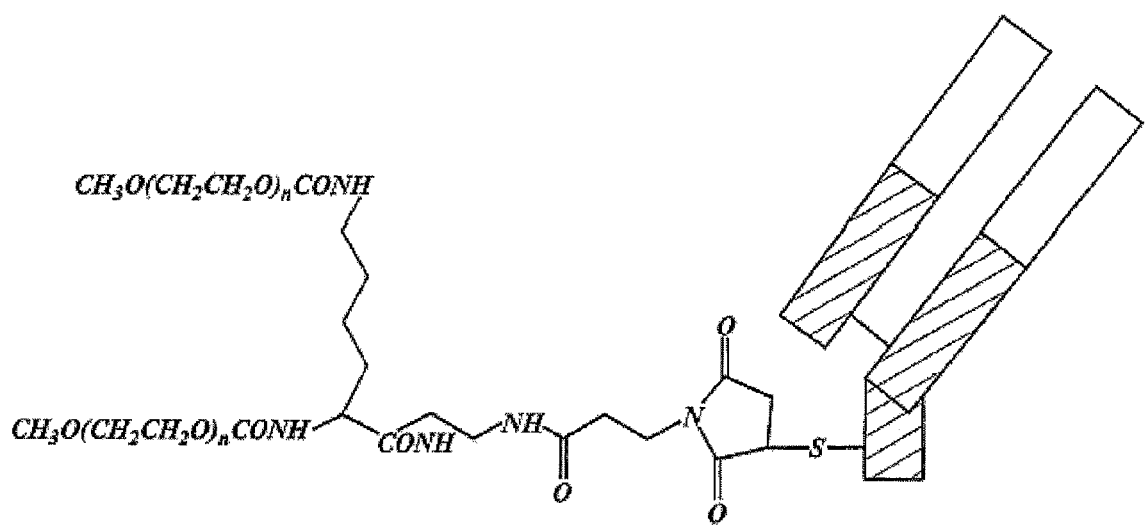

FIG. 12 shows the structure of a modified Fab fragment derived from an antibody to IL-1β covalently linked via a cysteine residue to a lysyl-maleimide linker wherein each amino group on the lysyl residue has covalently attached to it a methoxy PEG residue wherein n is about 420.

DNA MANIPULATIONS AND GENERAL METHODS

E. coli strain INVαF' (Invitrogen) was used for transformation and routine culture growth. DNA restriction and modification enzymes were obtained from Roche Diagnostics Ltd. and New England Biolabs. Plasmid preparations were performed using Maxi Plasmid purification kits (QIAGEN, catalogue No. 12165). DNA sequencing reactions were performed using the ABI Prism Big Dye terminator sequencing kit (catalogue No. 4304149) and run on an ABI 3100 automated sequencer (Applied Biosystems). Data was analysed using the program AutoAssembler (Applied Biosystems). Oligonucleotides were obtained from OSWEL. The concentration of Fab' was determined using Fab' assembly ELISA.

EXAMPLE 1

Gene Cloning and Expression of the Variable Regions from Murine Monoclonal Antibody IC8

Preparation of Total RNA

The hybridoma expressing IC8 was generated by Cistron using conventional hybridoma technology following immunisation of mice with human IL-1β protein. The hyriboma was then obtained by Celltech R&D Limited. Total RNA was prepared from IC8 hybridoma cells using the QIAGEN RNeasy kit (QIAGEN Ltd, catalogue no. 74104). The RNA obtained was reverse transcribed to cDNA using the Clontech cDNA Advantage RT for PCR kit (catalogue no. K1402).

PCR Cloning of IC8 VH and VL Regions

The cDNA prepared from hybridoma cells was used as the template for PCR in a series of reactions designed to amplify the V-region sequences. The reactions used a set of 'forward' degenerate primers designed to anneal to DNA within the conserved signal sequence, and a reverse primer annealing to DNA encoding the framework 4/constant region junction. PCR was performed using Taq Plus Precision (Stratagene, catalogue No. 600211) and a 0.25 mM concentration of dNTP. The resultant PCR products were cloned into sequencing vectors (InVitrogen Zero Blunt TOPO PCR cloning kit for sequencing, catalogue No. K2875) and the DNA sequence was determined. N-terminal protein sequencing of the purified IC8 antibody (from the hybridoma) was used to confirm that the translated sequences corresponded to the observed protein sequence. The V-region sequences are shown in FIG. 1 and in SEQ ID NOS:1 to 4.

Figure 2:
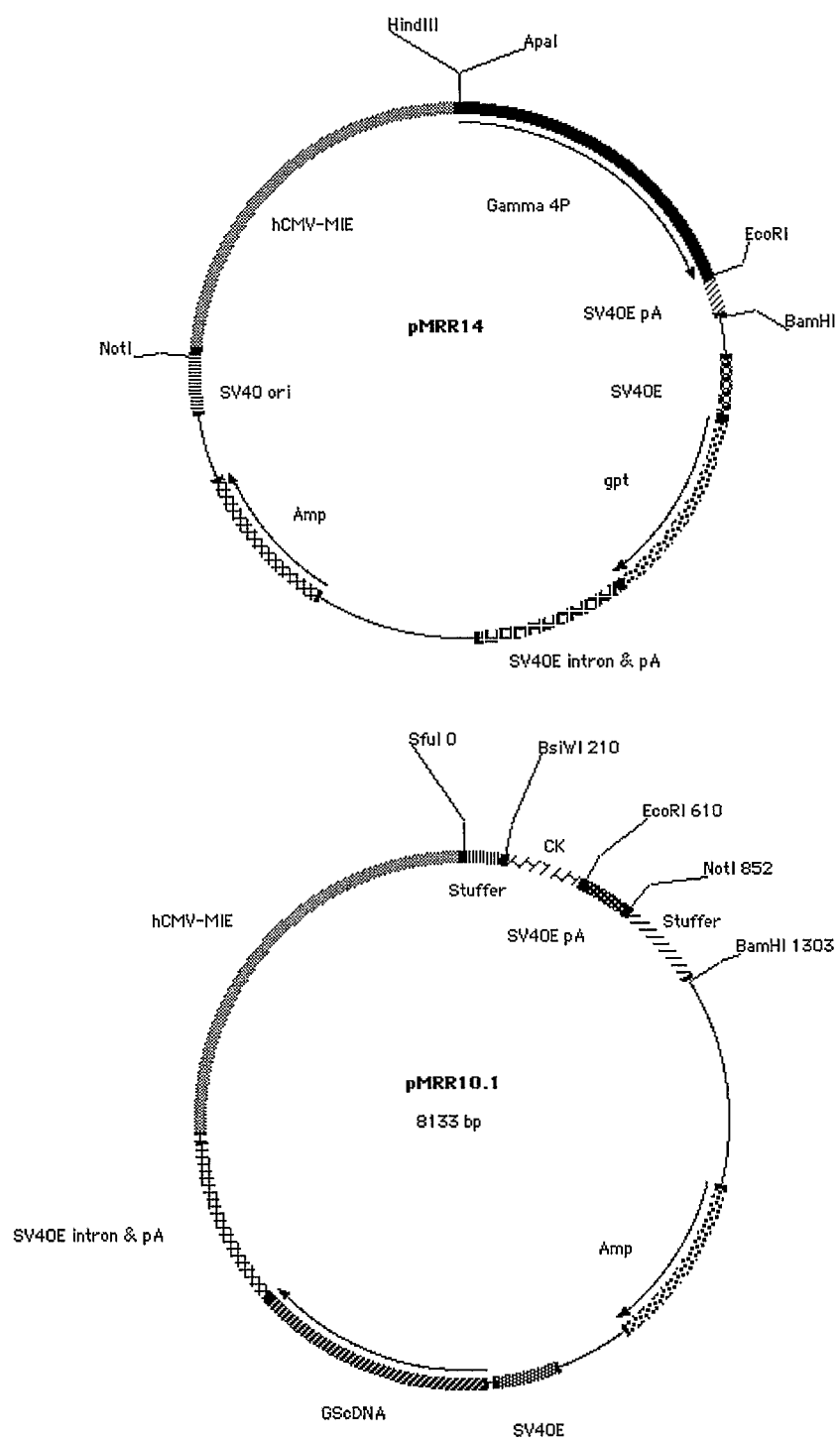

The murine V-region genes were then sub-cloned into the expression vectors pMRR10 and pMRR14 (FIG. 2). These are separate vectors for expression of the light and heavy chain respectively and contain genomic DNA encoding constant region genes for human kappa light chain and gamma-4 heavy chain respectively.

The double chimeric IC8 antibody molecule cHcL was expressed by transient co-transfection of the heavy and light chain expression vectors described above (pMRR10 and pMRR14 containing IC8 VL and VH respectively) into CHO-L761 cells. Transfections were performed using the lipofectamine procedure according to manufacturer's instructions (InVitrogen, catalogue No. 18324).

EXAMPLE 2

CDR-Grafting of IC8

The CDRs from IC8 were CDR-grafted into human frameworks in order to reduce potential immunogenicity and to facilitate E. coli expression. Human germline acceptor frameworks were chosen from sub-groups VH3 and VK1. FIG. 3 shows an alignment between the donor mouse sequence and the acceptor human frameworks. The heavy chain acceptor framework is the human germline sequence VH3-11 (DP-35), with framework 4 coming from this portion of the human JH-region germline JH4. The light chain acceptor framework is the human germline sequence O12 (DPK9), with framework 4 coming from this portion of the human JK-region germline JK1.

The alignment in FIG. 3 shows that there are 13 framework differences between the donor and acceptor heavy chains (excluding CDRs). At each of these positions an analysis was made of the potential of that residue to contribute to antigen binding, through direct contact with antigen, through a role in CDR packing, or through involvement at the VL/VH interface; if considered important, the murine donor residue was retained. The light chain alignment shows that there are 15 framework differences between the donor and acceptor sequences (excluding CDRs). The potential of the murine residue to contribute to antigen binding was again analysed. In this way, three VH grafts and three VL grafts were designed. These are also shown in FIG. 3 and correspond to SEQ ID NO:13 (gH1), SEQ ID NO:14 (gH2), SEQ ID NO:15 (gH3), SEQ ID NO:18 (gL1), SEQ ID NO:19 (gL2) and SEQ ID NO:20 (gL3).

EXAMPLE 3

Design and Construction of Genes for Grafted Sequences

Genes were designed to encode the grafted sequences, using codons frequently used in E. coli and avoiding 'rare' E. coli codons (Wada et al. (1991), Nucl. Acids Res., 19, 1981-86). Restriction sites were introduced into the DNA sequence at intervals to facilitate further genetic manipulation. FIG. 4 shows the design of genes for gH1 and gL1, the sequences of which are given in SEQ ID NOS:21 and 22. The corresponding amino acid sequences are given in SEQ ID NOS:23 and 24, respectively.

Completely overlapping oligonucleotides were used to construct the genes encoding gH1 and gL1 (FIG. 5; SEQ ID NOS:27-58). The oligonucleotides encoding the designed genes were annealed together by mixing at a concentration of 100 pmoles/μl in buffer (12.5 mM TrisHCl pH 7.5, 2.5 mM MgCl$_2$, 25 mM NaCl, 0.25 mM dithioerythritol) and heating to 95° C. for 3 minutes in a PCR block programmed to cool down to 30° C. at a rate of −0.01° C. every 10 seconds. T4 DNA ligase (5 U) and its appropriate reaction buffer were added, and the oligonucleotides were ligated together by incubation at 25° C. for 1 hour. The ligated heavy and light chain genes were then amplified by PCR following addition of a 10-fold excess of 'end' primers T1 (SEQ ID NO:25) and B1 (SEQ ID NO:26). A proof-reading DNA polymerase was used for this amplification (Taq Plus Precision, Stratagene). Amplification products were run on a 1.5% agarose gel. The 400-450 band was isolated and gel purified then cloned into the intermediate vector pCR4 blunt TOPO according to the manufacturer's instructions (InVitrogen). This created the intermediate plasmids pCR4(IC8gL1) and pCR4(IC8gH1). These plasmids were then used as the templates to create the further grafted forms gL2, gL3, gH2 and gH3.

An oligonucleotide cassette replacement method was used to create the humanised grafts gL2 and gL3. FIG. 6 shows the design of the oligonucleotide cassettes. To construct each variant, the vector pCR4(IC8gL1) was cut with the restriction enzymes KpnI and NheI. The resulting large vector fragment was gel purified from agarose and was used in ligation with the oligonucleotide cassette. Oligonucleotide pairs were annealed together by mixing at a concentration of 0.5 pmoles/µl in a volume of 200 µl buffer (12.5 mM TrisHCl pH 7.5, 2.5 mM MgCl$_2$, 25 mM NaCl, 0.25 mM dithioerythritol), and heating to 95° C. for 3 minutes in a waterbath (volume 500 ml) then allowed to slow-cool to room temperature. The annealed oligonucleotide cassette was then diluted ten-fold in water before ligation into the appropriately cut vector. DNA sequencing was used to confirm the correct sequence, creating plasmids pCR4(IC8gL2) and pCR4(IC8gL3).

The variant gH2 was constructed from pCR4(IC8gH1) using a PCR strategy. The reverse strand of the cassette shown in FIG. 6 (SEQ ID NO:64) was used as a reverse primer in PCR using a vector specific 5' forward primer to generate a product representing the partial gH2 sequence. This was digested with restriction enzymes HindIII and BspEI then cloned into HindIII-BspEI restricted pCR4(IC8gH1) to create pCR4(IC8gH2).

The variant gH3 was constructed using a different PCR strategy. The two gH3 oligos shown in FIG. 6 were used in separate PCR reactions: the sense strand (SEQ ID NO:66) as a forward primer using a vector-specific 3' reverse primer, and the non-sense strand (SEQ ID NO:67) as a reverse primer using a vector-specific 5' forward primer. In both cases the template was pCR4(IC8gH1). The two resulting amplification products were isolated and purified, then added together with both 5' and 3' vector-specific primers and cycled through additional PCR amplifications to generate a full length gH3 product. This was digested with HindIII and ApaI and inserted into pCR4(IC8gH1) restricted with HindIII-ApaI, to create pCR4(IC8gH3). All variants were confirmed by DNA sequencing.

Each of the heavy chain grafts was then sub-cloned into the expression vector pMRR14 as HindIII-ApaI fragments. Each of the 3 light chain grafts was sub-cloned into the light chain expression vector pMRR10 as SfuI-BsiWI fragments.

Selection of Optimum Grafted Variant

The grafted antibodies were expressed by transient co-transfection of the grafted heavy and light chain expression vectors described above (pMRR10 and pMRR14 containing IC8 gL1, gL2 and gL3 and gH1, gH2 and gH3 respectively) into CHO-L761 cells. Transfections were performed using the lipofectamine procedure according to manufacturer's instructions (InVitrogen, catalogue no. 18324).

All combinations of grafted chain and chimeric chain were expressed and compared against the double chimeric antibody cHcL. Binding was assessed in a BIAcore assay and in an IL-1β neutralisation assay.

BIAcore Assay

The assay format used anti-IL-1β antibody captured by anti-hFc with a titration of recombinant human IL-1β in the solution phase. Mouse anti-human IgG, Fc fragment-specific (Celltech) was immobilised on flowcell 2 of a CM5 Sensor Chip via amine coupling chemistry to a level of 12757RU. A blocked reference surface was prepared on flowcell 1 by activation with EDC/NHS and deactivation with ethanolamine using the same volumes as for flowcell 2. HBS-EP buffer (10 mM HEPES pH 7.4, 0.15 M NaCl, 3 mM EDTA, 0.005% Surfactant P20, Biacore AB) was used as the running buffer and assays were performed at 25° C. Anti-IL-1β antibody was passed over flowcells 1 and 2 and captured on the immobilised anti-hFc surface using a flowrate of 10 µl/min. IL-1β from 400-0 nM was injected over the blocked and captured anti-IL-1β antibody surface using a flowrate of 30 µl/min for 3 min. The anti-hFc surface was regenerated with a 30 µl injection of 40 mM HCl. Kinetic parameters were calculated using BIAevaluation 3.1 software.

For gIC8 Fab', the assay format used anti-IL-1β antibody captured by anti-hF(ab')$_2$ (where 'h' indicates that it is a human F(ab')$_2$) then IL-1β titrated over. Affinipure goat anti-human IgG, F(ab')$_2$ fragment-specific (Jackson ImmunoResearch Code 109-005-097) was immobilised on flowcell 2 of a CM5 Sensor Chip via amine coupling chemistry to a level of 13025RU. A blocked reference surface was prepared on flowcell 1 by activation with EDC/NHS and deactivation with ethanolaomine using the same volumes as for flowcell 2. HBS-EP buffer (10 mM HEPES pH 7.4, 0.15 M NaCl, 3 mM EDTA, 0.005% Surfactant P20, Biacore AB) was used as the running buffer and assays were performed at 25° C. Anti-IL-1β antibody was passed over flowcells 1 and 2 and captured on the immobilised anti-hF(ab')$_2$ surface using a flowrate of 10 µl/min. IL-1β (Strathmann) from 400-0 nM was injected over the blocked and captured anti-IL-1β antibody surface using a flowrate of 30 µl/min for 3 min. The anti-hF(ab')$_2$ surface was regenerated with a 30 µl injection of 40 mM HCl followed by a 15 µl injection of 5 mM NaOH. Kinetic parameters were calculated using BIAevalutation 3.1 software.

Table 1 shows a summary of Biacore antigen affinity data. It is clear that the gH1 graft, which has donor residues at positions 44 and 89, has a higher affinity than gH2, which only has a donor residue at position 89. The gH2 graft was, therefore, rejected. Surprisingly, high affinity was observed in the gH3 graft in which only position 44 is a donor framework residue.

TABLE 1

| Affinity by BIAcore | |
|---|---|
| Anti-IL-1β | $K_D$ (nM) |
| mIC8 | 0.30 |
| cHcL | 0.38 |
| gH1gL1 | 0.35 |
| gH1gL2 | 0.34 |
| gH1gL3 | 0.30 |
| gH2gL1 | 1.27 |
| gH2gL3 | 1.14 |
| gH2gL3 | 1.07 |
| gH3gL1 | 0.28 |
| gH3gL2 | 0.32 |
| gH3gL3 | 0.28 |
| gH3gL3 Fab' | 0.32 |

In Vitro Neutralisation Assay

Fibroblasts were grown to 80% confluence in 96 well plates. Antibodies were titrated in half log dilutions from 1 µg/ml and IL-1β was added to give 20 pg/ml final concentration. The plates were incubated at room temperature for 30 min. Culture medium was removed from fibroblast cultures and 100 µl antibody/IL-1β mix added to the appropriate wells and cultured overnight at 37° C. The amount of IL-6 produced in response to IL-1β was then estimated using the R&D Systems Human IL-6 Duoset Kit DY206.

The results of the neutralisation assay are shown in FIG. 7, in which the grafted forms of the antibody (excluding gH2) are compared with the parent mouse antibody. As with the Biacore affinity data there is very little difference between any of the remaining grafts. Hence gL3gH3 was selected as the variant with optimum activity and the fewest number of mouse framework residues. As shown in FIG. 3, the gH3 sequence has 1 donor framework residue, whilst the gL3 sequence has 3 donor framework residues.

In Vivo Neutralisation Assay

To determine the neutralisation efficacy of the gH3gL3Fab' in vivo, the gH3gL3Fab' was tested in two in vivo models of inflammation.

Intraperitoneal gH3gL3Fab'-PEG(40K)/Intraperitoneal hIL-1β in Mice

Male Balb/c mice (18-25 g) were injected intraperitoneally (i.p.) with gH3gL3Fab'-PEG(40K) (100 µl, in PBS vehicle) or control Fab'-PEG(40K) (100 µl, in PBS vehicle) 5 minutes prior to i.p. injection with hIL-1β (150 ng/kg) or vehicle (100 µl PBS). After 120 minutes, mice were killed by cervical dislocation and peritoneal lavage performed (3 ml HBSS (Hanks' Balanced Salts)+0.25% BSA, 12 mM HEPES). A total leukocyte count was performed using a Coulter Counter. For identification of neutrophils, 50 µl peritoneal lavage fluid was stained with 1:300 dilution of anti-CD45-CyChrome mAb and 1:300 dilution of anti phycoerythrin labelled GR-1 mAb (anti-Ly6G/Ly6C) for 20 min (4° C., in dark). Leukocytes were washed once in HBSS (0.25% BSA, 12 mM HEPES), resuspended in 300 µl HBSS (0.25% BSA, 12 mM HEPES) and analysed by flow cytometry. Neutrophils were identified as $CD45^+GR-1^{HIGH}$. Murine monocyte chemoattractant protein-1 (mMCP-1) concentration in the peritoneal lavage samples was measured by sandwich ELISA according to the manufacturer's instructions (BD Biosciences OPT-EIA mMCP-1).

Intravenous gH3gL3 Fab'-PEG(40K)/Intravenous hIL-1β in Mice

Male Balb/c mice (18-25 g) were anaesthetised with halothane and injected intravenously (i.v.) with gH3gL3Fab'-PEG(40K) (100 µl, in PBS vehicle) or control Fab-PEG (100 µl, in PBS vehicle) 15 minutes prior to i.v. injection with hIL-1β (37.5 or 50 µg/kg) or vehicle (100 µl PBS). After 90 minutes, a blood sample was taken by cardiac puncture into heparin (20 µl, 100 U/ml), and plasma was prepared by centrifugation (14,000×g, 2 min, RT). Plasma samples were stored at −20° C. Plasma samples were assayed for murine interleukin-6 (mIL-6) by sandwich ELISA according to the manufacturer's instructions (BD Biosciences OPT-EIA mIL-6).

The results demonstrate that the pre-treatment of mice with i.p. gH3gL3Fab'PEG(40K) was effective in reducing i.p. hIL-1β-induced neutrophil accumulation (Table 2) and mMCP-1 generation (Table 3). The pre-treatment of mice with i.v. gH3gL3Fab'-PEG (40K) was also effective in reducing i.v. hIL-1β-induced mIL-6 generation. Data from 3 separate experiments are summarised in Table 4.

No ill effects were observed at any of the doses used in either model. The antibody gH3gL3Fab' can, therefore, be expected to be useful in the treatment of inflammation and other IL-1β mediated diseases.

TABLE 2

| Neutrophil accumulation | | |
|---|---|---|
| Dose hIL-1β i.p. (ng/kg) | gH3gL3Fab'-PEG(40K) $ED_{50}$ (mg/kg) | Max inhibition (%, dose, mg/kg) |
| 150 | 0.02 | 96 (1) |
| 150 | 0.02 | 97 (1) |
| 150 | 0.03 | 95 (1) |
| 150 | 0.06 | 86 (0.1) |
| 150 | 0.03 | 89 (1) |
| 150 | 0.03 | 98 (0.3) |

TABLE 3

| mMCP-1 generation | | |
|---|---|---|
| Dose hIL-1β i.p. (ng/kg) | gH3gL3Fab'-PEG(40K) $ED_{50}$ (mg/kg) | Max inhibition (%, dose, mg/kg) |
| 150 | 0.02 | 98 (1) |
| 150 | 0.01 | 100 (1) |
| 150 | 0.02 | 98 (1) |
| 150 | 0.04 | 92 (1) |
| 150 | 0.02 | 98 (1) |
| 150 | NA | 99 (0.3) |

TABLE 4

| Dose hIL-1β i.v. (ng/kg) | gH3gL3Fab'-PEG(40K) $ED_{50}$ (mg/kg) | Max inhibition (%, dose, mg/kg) |
|---|---|---|
| 50 | 1.88 | 75 (10) |
| 37.5 | 5.39 | 81 (10) |
| 37.5 | 2.95 | 86 (10) |

EXAMPLE 4

Cloning and Expression of Fab' Fragments

Cloning of Selected V-Regions into *E. coli* Fab' Expression Plasmid pTTOD(Fab')

The expression vector containing an irrelevant Fab', termed pTTOD(Fab'), is shown in FIG. 8. The DNA encoding both the light chain and heavy chain is preceded by DNA encoding the *E. coli* OmpA signal sequence (Movva N R, Nakamura K and Inouye M. Amino acid sequence of the signal peptide of ompA protein, a major outer membrane protein of *Escherichia coli*. J Biol. Chem. 1980; 255(1): 27-9). The V-regions of IC8 were cloned into this vector so that this signal sequence is maintained, directing the translocation of both chains to the *E. coli* periplasm. The signal peptide is cleaved on translocation, so that it does not form part of the product Fab' sequence. (note; the sequence of the OmpA signal peptide is amino acid residues 1 to 21 of the sequence given in SEQ ID NO:70. Plasmid pTTOD(Fab') was digested with restriction enzymes EcoRV and BsiWI (BsiWI and SplI are isoschizomers) to remove the irrelevant VL sequence and the IC8 gL3 V-region was inserted, following its isolation from pMRR10(IC8gL3). This created the cloning intermediate pTTOD(IC8gL3). pTTOD(IC8gL3) was then cleaved with BsiWI and ApaI and 2 fragments were inserted in a 3-way ligation; a c-kappa/IGS-fragment (either IGS-2 or IGS-3) and the IC8gH3 fragment (see schematic representation in FIG. 9). In this way, the 2 vector variants pTTOD(IC8gL3gH3 IGS-2) and pTTOD (IC8gL3gH3 IGS-3) were constructed. These vary only in the nucleotide sequence between the light and heavy chain genes: IGS-2 confers very tight translational coupling between the 2 genes giving a rapid rate of heavy chain translation, IGS-3 confers a slower rate of heavy chain translation (see UK patent application No. 0129105).

Fermenter Expression of Fab' in E. Coli

Plasmids pTTOD(IC8gL3gH3 IGS-2) and pTTOD (IC8gL3gH3 IGS-3) were transformed into the E. coli strain W3110 using standard protocols. The soluble E. coli periplasmic Fab' was extracted using tris-EDTA buffer at 50° C. After extraction & cooling, the pH of the extract was adjusted and the cells removed by centrifugation and filtration. The clarified feedstream was diluted with water (approx 2-fold) in order to reduce the conductivity. Fab' was captured using cation-exchange chromatography (SP sepharose FF resin) and bound Fab' eluted using a NaCl step. The eluted product stream was concentrated, diafiltered into tris buffer using ultrafiltration and subjected to anion-exchange chromatography (Q sepharose FF resin) where the Fab' was contained in the unbound fraction. The purified Fab' was concentrated & diafiltered into reduction buffer (by ultrafiltration) followed by reduction using 2-mercaptoethylamine to activate the hinge thiol. The reductant is then removed by ultrafiltration buffer-exchange. N-terminal sequencing confirmed the correct amino acid sequence and cleavage of the OmpA leader. Expression of Fab' by these two plasmids was compared.

Table 5 shows a comparison of fermenter Fab' yields for the IGS-2 and the IGS-3 variants. The IGS-2 construct clearly out-performs IGS-3 for Fab' productivity. Therefore the IGS-2 variant was selected. The plasmid map is shown in FIG. 10. FIG. 11 shows the Fab' coding and flanking sequence of pTTOD(gH3gL3 Fab' IGS-2).

TABLE 5

Fermenter expression yields; a comparison of anti IL-1B gIC8 periplasmic Fab' yields

| Fermentations | Date | Construct | Peri. Fab' ELISA (mg/l) | Protein G A280 (mg/l) |
|---|---|---|---|---|
| FM264 | Sep. 25, 2001 | gIC8 IGS2 | 602 | 588 |

TABLE 5-continued

Fermenter expression yields; a comparison of anti IL-1B gIC8 periplasmic Fab' yields

| Fermentations | Date | Construct | Peri. Fab' ELISA (mg/l) | Protein G A280 (mg/l) |
|---|---|---|---|---|
| FM265 | Sep. 25, 2001 | gIC8 IGS2 | 742 | 533 |
| FM266 | Sep. 25, 2001 | gIC8 IGS3 | 243 | |
| FM267 | Sep. 25, 2001 | gIC8 IGS3 | 224 | |

Activity of E. coli-Produced Fab'

Some of the purified E. coli-produced Fab' was then analysed for affinity in the Biacore assay, as shown in Table 1. As can be seen, this material retains effectively full activity in this assay.

PEGylation of the Fab

The purified modified Fab is site-specifically conjugated with a branched molecule of PEG. This is achieved by activation of a single cysteine residue in a truncated hinge region of the modified Fab, followed by reaction with (PEG)-lysyl maleimide as previously described (A. P. Chapman et al., Nature Biotechnology 17, 780-783, 1999). A PEGylated molecule of the invention is represented in FIG. 12. The PEG used was 20K methoxy-PEG-amine (obtainable from Nektar, formerly Shearwater). The resulting Fab'-PEG was purified by cation-exchange chromatography (SP sepharose HP) using a linear NaCl gradient elution. Purified Fab'-PEG was concentrated and formulated by ultrafiltration into 50 mM sodium acetate+125 mM NaCl, pH 5.5 to produce the therapeutic neutralising antibody of the invention.

It will of course be understood that the present invention has been described by way of example only, is in no way meant to be limiting, and that modifications of detail can be made within the scope of the claims hereinafter. Preferred features of each embodiment of the invention are as for each of the other embodiments mutatis mutandis. All publications, including but not limited to patents and patent applications, cited in this specification are herein incorporated by reference as if each individual publication were specifically and individually indicated to be incorporated by reference herein as though fully set forth.

The invention claimed is:

1. A method for the treatment of inflammation mediated by IL-1β or associated with an increased level of IL-1β comprising administering to a patient suffering from such inflammation a pharmaceutically effective amount of a pharmaceutical composition, said composition comprising a neutralising antibody having specificity for human IL-1β, the antibody comprising a heavy chain and a light chain, wherein the variable domain of the heavy chain comprises the sequence given in SEQ ID NO:5 for CDR-H1, the sequence given in SEQ ID NO:6 for CDR-H2 and the sequence given in SEQ ID NO:7 for CDR-H3 and wherein the variable domain of the light chain comprises the sequence given in SEQ ID NO:8 for CDR-L1, the sequence given in SEQ ID NO:9 for CDR-L2 and the sequence given in SEQ ID NO:10 for CDR-L3, in combination with one or more of a pharmaceutically acceptable excipient, diluent or carrier.

2. The method of claim 1 wherein the inflammation is associated with a viral infection, a bacterial infection, a fungal infection, a parasitic infection, endotoxic shock associated with infection, arthritis, rheumatoid arthritis, pelvic inflammatory disease, Alzheimer's Disease, Crohn's disease, Peyronie's Disease, coeliac disease, gallbladder disease, Pilonidal disease, peritonitis, meningoencephalitis, pancreatitis, trauma caused by surgery, graft-versus-host disease, transplant rejection, melanomas, hepatoblastomas, sarcomas, squamous cell carcinomas, transitional cell cancers, ovarian cancers, hematologic malignancies, acute myelogenous leukaemia, chronic myelogenous leukemia, gastric cancer, colon cancer, heart disease, myocardial infarction, atherosclerosis, intravascular coagulation, bone resorption, osteoporosis, periodontitis, or hypochlorhydia.

3. The method of claim 1, wherein said neutralising antibody is a CDR-grafted antibody molecule.

4. The method of claim 1, wherein the variable domain of either the heavy chain, the light chain, or both the heavy chain and the light chain comprises human acceptor framework regions and non-human donor CDRs.

5. The method of claim 1, wherein the heavy chain comprises the sequence gH3 (SEQ ID NO: 15).

6. The method of claim 1, wherein the light chain comprises the sequence gL3 (SEQ ID NO: 20).

7. The method of claim 1, wherein the heavy chain comprises the sequence gH3 (SEQ ID NO: 15) and the light chain comprises the sequence gL3 (SEQ ID NO: 20).

8. The method of claim 1, wherein the antibody molecule is selected from the group consisting of: a complete antibody molecule having full length heavy and light chains, a Fab, Fab', F(ab')$_2$, Fv fragment, scFv fragment, and Fab that has been modified to enable an effector or reporter molecule to be attached to it, wherein the modification is the addition to the C-terminal end of its heavy chain of one or more amino acids to allow the attachment of an effector or reporter molecule.

9. The method of claim 8, wherein the additional amino acids form a modified hinge region containing one or two cysteine residues to which the effector or reporter molecule may be attached.

10. The method of claim 8, wherein said neutralising antibody molecule has an effector or a reporter molecule attached to it.

11. The method of claim 10 wherein the effector molecule comprises one or more polymers.

12. The method of claim 11, wherein the one or more polymers is/are optionally substituted straight or branched chain polyalkylene, polyalkenylene or polyoxyalkylene polymer or a branched or unbranched polysaccharide.

13. The method of claim 11, wherein the one or more polymers is/are a methoxypoly(ethyleneglycol) or poly(ethyleneglycol).

14. The method of claim 11, wherein said neutralising antibody molecule has attached to one of the cysteine residues at the C-terminal end of the heavy chain a lysyl-maleimide or lysyl bis-maleimide group wherein each amino group of the lysyl residue has covalently linked to it a methoxypoly(ethyleneglycol) residue having a molecular weight of about 20,000 Da.

15. A method for the treatment of inflammation mediated by IL-1β or associated with an increased level of IL-1β comprising administering to a patient suffering from such inflammation a pharmaceutically effective amount of a pharmaceutical composition, said composition comprising a neutralising antibody having specificity for human IL-1β, having a heavy chain comprising the sequence given in SEQ ID NO: 3 and a light chain comprising the sequence given in SEQ ID NO:4.

16. A method for the treatment of inflammation mediated by IL-1β or associated with an increased level of IL-1β comprising administering to a patient suffering from such inflammation a pharmaceutically effective amount of a pharmaceutical composition, said composition comprising a neutralising antibody having specificity for human IL-1β, which antibody is a modified Fab fragment having a heavy chain comprising the sequence given in SEQ ID NO: 15 and a light chain comprising the sequence given in SEQ ID NO:20 and having at the C-terminal end of its heavy chain a modified hinge region containing one cysteine residue to which an effector or reporter molecule may be attached.

17. A method for the treatment of inflammation mediated by IL-1β or associated with an increased level of IL-1β comprising administering to a patient suffering from such inflammation a pharmaceutically effective amount of a pharmaceutical composition, said composition comprising a neutralising antibody having specificity for human IL-1β, which antibody is a modified Fab fragment having a heavy chain comprising the sequence given in SEQ ID NO: 15 and a light chain comprising the sequence given in SEQ ID NO:20 and having at the C-terminal end of its heavy chain a modified hinge region containing one cysteine residue to which an effector or reporter molecule is attached.

18. A method for the treatment of inflammation mediated by IL-1β or associated with an increased level of IL-1β comprising administering to a patient suffering from such inflammation a pharmaceutically effective amount of a pharmaceutical composition, said composition comprising a neutralising antibody having specificity for human IL-1β having a heavy chain comprising amino acid residue numbers 22 to 251 of the sequence given in SEQ ID NO:71 and a light chain comprising amino acid residue numbers 22 to 235 of the sequence given in SEQ ID NO:70 and having an effector or reporter molecule attached to the cysteine residue at the C-terminal end of the heavy chain.

19. The method of claim 17 or 18, wherein said antibody has attached to the cysteine residue at the C-terminal end of the heavy chain a lysyl-maleimide group, wherein each amino group of the lysyl residue has covalently linked to it a methoxypoly(ethyleneglycol) residue having a molecular weight of about 20,000 Da.

20. The method of claim 19 wherein said antibody has the formula

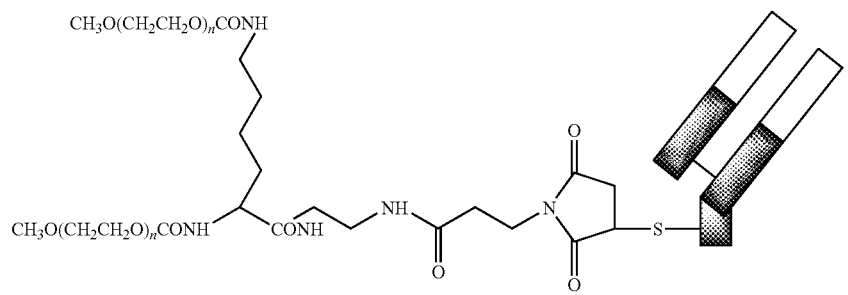

wherein n is about 420.

* * * * *

SEQUENCE LISTING

```
<160> NUMBER OF SEQ ID NOS: 75

<210> SEQ ID NO 1
<211> LENGTH: 414
<212> TYPE: DNA
<213> ORGANISM: Mus musculus

<400> SEQUENCE: 1
atggactttg ggctcagctt gatttteett gtecttactt taaaaggtgt gcagtgtgat      60
gtgcagttgg tggagtctgg gggaggctta gtgaagcctg gagggtccct gaaactctcc     120
tgtgcagcct ctggattcga tttcagtagg tatgacatgt cttgggttcg ccagactccg     180
gagaagaggc tggagtgggt cgcatatatt agtagtggtg gtggtagcac ctactttcca     240
gacactgtga agggccgatt caccatctcc agagacaatg ccaagaacac cctgtacctg     300
caaatgaaca atctgcagtc tgaggacaca gccatgtttt actgtgcaag acagaacaag     360
aaattaacct ggtttgatta ctggggccag gggactctgg tcactgtctc ttca           414
```

<210> SEQ ID NO 2
<211> LENGTH: 384
<212> TYPE: DNA
<213> ORGANISM: Mus musculus

<400> SEQUENCE: 2

```
atgagtgtgc tcactcaggt cctggcgttg ctgctgctgt ggcttgcagg tgccagatgt      60
gacatccaga tgactcagtc tccagcctcc ctatctgcat ctgtgggaga aactgtcacc     120
atcacatgtc gaacaagtgg gaatattcac aattatttaa catggtatca acagaatttg     180
ggaaaatctc ctcagctcct ggtctataat gcaaaaacct agcagatgg tgtgccatca      240
aggttcagtg gcagtggatc aggaacacaa ttttctctca cgatcaacag cctgcagcct     300
gaagattttg ggaattatta ctgtcaacat ttttggagtc ttccattcac gttcggctcg     360
gggacaaagt tggaaataaa acgt                                            384
```

<210> SEQ ID NO 3
<211> LENGTH: 138
<212> TYPE: PRT
<213> ORGANISM: Mus musculus

<400> SEQUENCE: 3

Met Asp Phe Gly Leu Ser Leu Ile Phe Leu Val Leu Thr Leu Lys Gly
1               5                   10                  15

Val Gln Cys Asp Val Gln Leu Val Glu Ser Gly Gly Gly Leu Val Lys
                20                  25                  30

Pro Gly Gly Ser Leu Lys Leu Ser Cys Ala Ala Ser Gly Phe Asp Phe
            35                  40                  45

Ser Arg Tyr Asp Met Ser Trp Val Arg Gln Thr Pro Glu Lys Arg Leu
        50                  55                  60

Glu Trp Val Ala Tyr Ile Ser Ser Gly Gly Gly Ser Thr Tyr Phe Pro
65                  70                  75                  80

Asp Thr Val Lys Gly Arg Phe Thr Ile Ser Arg Asp Asn Ala Lys Asn
                85                  90                  95

Thr Leu Tyr Leu Gln Met Asn Asn Leu Gln Ser Glu Asp Thr Ala Met
            100                 105                 110

Phe Tyr Cys Ala Arg Gln Asn Lys Lys Leu Thr Trp Phe Asp Tyr Trp
        115                 120                 125

Gly Gln Gly Thr Leu Val Thr Val Ser Ser
    130                 135

<210> SEQ ID NO 4
<211> LENGTH: 128
<212> TYPE: PRT
<213> ORGANISM: Mus musculus

<400> SEQUENCE: 4

Met Ser Val Leu Thr Gln Val Leu Ala Leu Leu Leu Trp Leu Ala
1               5                   10                  15

Gly Ala Arg Cys Asp Ile Gln Met Thr Gln Ser Pro Ala Ser Leu Ser
                20                  25                  30

Ala Ser Val Gly Glu Thr Val Thr Ile Thr Cys Arg Thr Ser Gly Asn
            35                  40                  45

Ile His Asn Tyr Leu Thr Trp Tyr Gln Gln Asn Leu Gly Lys Ser Pro
        50                  55                  60

Gln Leu Leu Val Tyr Asn Ala Lys Thr Leu Ala Asp Gly Val Pro Ser
65                  70                  75                  80

```
Arg Phe Ser Gly Ser Gly Ser Gly Thr Gln Phe Ser Leu Thr Ile Asn
                85                  90                  95

Ser Leu Gln Pro Glu Asp Phe Gly Asn Tyr Tyr Cys Gln His Phe Trp
            100                 105                 110

Ser Leu Pro Phe Thr Phe Gly Ser Gly Thr Lys Leu Glu Ile Lys Arg
        115                 120                 125
```

<210> SEQ ID NO 5
<211> LENGTH: 10
<212> TYPE: PRT
<213> ORGANISM: Mus musculus

<400> SEQUENCE: 5

```
Gly Phe Asp Phe Ser Arg Tyr Asp Met Ser
1               5                   10
```

<210> SEQ ID NO 6
<211> LENGTH: 17
<212> TYPE: PRT
<213> ORGANISM: Mus musculus

<400> SEQUENCE: 6

```
Tyr Ile Ser Ser Gly Gly Gly Ser Thr Tyr Phe Pro Asp Thr Val Lys
1               5                   10                  15

Gly
```

<210> SEQ ID NO 7
<211> LENGTH: 10
<212> TYPE: PRT
<213> ORGANISM: Mus musculus

<400> SEQUENCE: 7

```
Gln Asn Lys Lys Leu Thr Trp Phe Asp Tyr
1               5                   10
```

<210> SEQ ID NO 8
<211> LENGTH: 11
<212> TYPE: PRT
<213> ORGANISM: Mus musculus

<400> SEQUENCE: 8

```
Arg Thr Ser Gly Asn Ile His Asn Tyr Leu Thr
1               5                   10
```

<210> SEQ ID NO 9
<211> LENGTH: 7
<212> TYPE: PRT
<213> ORGANISM: Mus musculus

<400> SEQUENCE: 9

```
Asn Ala Lys Thr Leu Ala Asp
1               5
```

<210> SEQ ID NO 10
<211> LENGTH: 9
<212> TYPE: PRT
<213> ORGANISM: Mus musculus

<400> SEQUENCE: 10

```
Gln His Phe Trp Ser Leu Pro Phe Thr
1               5
```

<210> SEQ ID NO 11

```
<211> LENGTH: 119
<212> TYPE: PRT
<213> ORGANISM: Mus musculus

<400> SEQUENCE: 11

Asp Val Gln Leu Val Glu Ser Gly Gly Gly Leu Val Lys Pro Gly Gly
1               5                   10                  15

Ser Leu Lys Leu Ser Cys Ala Ala Ser Gly Phe Asp Phe Ser Arg Tyr
                20                  25                  30

Asp Met Ser Trp Val Arg Gln Thr Pro Glu Lys Arg Leu Glu Trp Val
            35                  40                  45

Ala Tyr Ile Ser Ser Gly Gly Ser Thr Tyr Phe Pro Asp Thr Val
    50                  55                  60

Lys Gly Arg Phe Thr Ile Ser Arg Asp Asn Ala Lys Asn Thr Leu Tyr
65                  70                  75                  80

Leu Gln Met Asn Asn Leu Gln Ser Glu Asp Thr Ala Met Phe Tyr Cys
                85                  90                  95

Ala Arg Gln Asn Lys Lys Leu Thr Trp Phe Asp Tyr Trp Gly Gln Gly
                100                 105                 110

Thr Leu Val Thr Val Ser Ser
        115

<210> SEQ ID NO 12
<211> LENGTH: 109
<212> TYPE: PRT
<213> ORGANISM: Homo sapiens

<400> SEQUENCE: 12

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
                20                  25                  30

Tyr Met Ser Trp Ile Arg Gln Ala Pro Gly Lys Gly Leu Glu Trp Val
            35                  40                  45

Ser Tyr Ile Ser Ser Ser Gly Ser Thr Ile Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Trp Gly Gln Gly Thr Leu Val Thr Val Ser Ser
                100                 105

<210> SEQ ID NO 13
<211> LENGTH: 119
<212> TYPE: PRT
<213> ORGANISM: Artificial Sequence
<220> FEATURE:
<223> OTHER INFORMATION: Synthetic Construct

<400> SEQUENCE: 13

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asp Phe Ser Arg Tyr
                20                  25                  30

Asp Met Ser Trp Val Arg Gln Ala Pro Gly Lys Arg Leu Glu Trp Val
            35                  40                  45

Ala Tyr Ile Ser Ser Gly Gly Ser Thr Tyr Phe Pro Asp Thr Val
    50                  55                  60
```

```
Lys Gly Arg Phe Thr Ile Ser Arg Asp Asn Ala Lys Asn Thr Leu Tyr
 65                  70                  75                  80

Leu Gln Met Asn Ser Leu Arg Ala Glu Asp Thr Ala Met Tyr Tyr Cys
                 85                  90                  95

Ala Arg Gln Asn Lys Lys Leu Thr Trp Phe Asp Tyr Trp Gly Gln Gly
            100                 105                 110

Thr Leu Val Thr Val Ser Ser
        115

<210> SEQ ID NO 14
<211> LENGTH: 119
<212> TYPE: PRT
<213> ORGANISM: Artificial Sequence
<220> FEATURE:
<223> OTHER INFORMATION: Synthetic Construct

<400> SEQUENCE: 14

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Asp Phe Ser Arg Tyr
             20                  25                  30

Asp Met Ser Trp Val Arg Gln Ala Pro Gly Lys Gly Leu Glu Trp Val
         35                  40                  45

Ala Tyr Ile Ser Ser Gly Gly Ser Thr Tyr Phe Pro Asp Thr Val
 50                  55                  60

Lys Gly Arg Phe Thr Ile Ser Arg Asp Asn Ala Lys Asn Thr Leu Tyr
 65                  70                  75                  80

Leu Gln Met Asn Ser Leu Arg Ala Glu Asp Thr Ala Met Tyr Tyr Cys
                 85                  90                  95

Ala Arg Gln Asn Lys Lys Leu Thr Trp Phe Asp Tyr Trp Gly Gln Gly
            100                 105                 110

Thr Leu Val Thr Val Ser Ser
        115

<210> SEQ ID NO 15
<211> LENGTH: 119
<212> TYPE: PRT
<213> ORGANISM: Artificial Sequence
<220> FEATURE:
<223> OTHER INFORMATION: Synthetic Construct

<400> SEQUENCE: 15

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Asp Phe Ser Arg Tyr
             20                  25                  30

Asp Met Ser Trp Val Arg Gln Ala Pro Gly Lys Arg Leu Glu Trp Val
         35                  40                  45

Ala Tyr Ile Ser Ser Gly Gly Gly Ser Thr Tyr Phe Pro Asp Thr Val
 50                  55                  60

Lys Gly Arg Phe Thr Ile Ser Arg Asp Asn Ala Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gln Asn Lys Lys Leu Thr Trp Phe Asp Tyr Trp Gly Gln Gly
            100                 105                 110

Thr Leu Val Thr Val Ser Ser
        115
```

<210> SEQ ID NO 16
<211> LENGTH: 108
<212> TYPE: PRT
<213> ORGANISM: Mus musculus

<400> SEQUENCE: 16

Asp Ile Gln Met Thr Gln Ser Pro Ala Ser Leu Ser Ala Ser Val Gly
1               5                   10                  15

Glu Thr Val Thr Ile Thr Cys Arg Thr Ser Gly Asn Ile His Asn Tyr
            20                  25                  30

Leu Thr Trp Tyr Gln Gln Asn Leu Gly Lys Ser Pro Gln Leu Leu Val
        35                  40                  45

Tyr Asn Ala Lys Thr Leu Ala Asp Gly Val Pro Ser Arg Phe Ser Gly
    50                  55                  60

Ser Gly Ser Gly Thr Gln Phe Ser Leu Thr Ile Asn Ser Leu Gln Pro
65                  70                  75                  80

Glu Asp Phe Gly Asn Tyr Tyr Cys Gln His Phe Trp Ser Leu Pro Phe
                85                  90                  95

Thr Phe Gly Ser Gly Thr Lys Leu Glu Ile Lys Arg
            100                 105

<210> SEQ ID NO 17
<211> LENGTH: 106
<212> TYPE: PRT
<213> ORGANISM: Homo sapiens

<400> SEQUENCE: 17

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Phe
                85                  90                  95

Gly Gln Gly Thr Lys Val Glu Ile Lys Arg
            100                 105

<210> SEQ ID NO 18
<211> LENGTH: 108
<212> TYPE: PRT
<213> ORGANISM: Artificial Sequence
<220> FEATURE:
<223> OTHER INFORMATION: Synthetic Construct

<400> SEQUENCE: 18

Asp Ile Gln Met Thr Gln Ser Pro Ser Ser Leu Ser Ala Ser Val Gly
1               5                   10                  15

Asp Arg Val Thr Ile Thr Cys Arg Thr Ser Gly Asn Ile His Asn Tyr
            20                  25                  30

Leu Thr Trp Tyr Gln Gln Lys Leu Gly Lys Ala Pro Gln Leu Leu Val
        35                  40                  45

Tyr Asn Ala Lys Thr Leu Ala Asp Gly Val Pro Ser Arg Phe Ser Gly
    50                  55                  60

```
Ser Gly Ser Gly Thr Gln Phe Thr Leu Thr Ile Ser Ser Leu Gln Pro
 65                  70                  75                  80

Glu Asp Phe Ala Asn Tyr Tyr Cys Gln His Phe Trp Ser Leu Pro Phe
             85                  90                  95

Thr Phe Gly Gln Gly Thr Lys Val Glu Ile Lys Arg
            100                 105

<210> SEQ ID NO 19
<211> LENGTH: 108
<212> TYPE: PRT
<213> ORGANISM: Artificial Sequence
<220> FEATURE:
<223> OTHER INFORMATION: Synthetic Construct

<400> SEQUENCE: 19

Asp Ile Gln Met Thr Gln Ser Pro Ser Ser Leu Ser Ala Ser Val Gly
 1               5                  10                  15

Asp Arg Val Thr Ile Thr Cys Arg Thr Ser Gly Asn Ile His Asn Tyr
             20                  25                  30

Leu Thr Trp Tyr Gln Gln Lys Pro Gly Lys Ala Pro Gln Leu Leu Val
         35                  40                  45

Tyr Asn Ala Lys Thr Leu Ala Asp Gly Val Pro Ser Arg Phe Ser Gly
     50                  55                  60

Ser Gly Ser Gly Thr Gln Phe Thr Leu Thr Ile Ser Ser Leu Gln Pro
 65                  70                  75                  80

Glu Asp Phe Ala Asn Tyr Tyr Cys Gln His Phe Trp Ser Leu Pro Phe
             85                  90                  95

Thr Phe Gly Gln Gly Thr Lys Val Glu Ile Lys Arg
            100                 105

<210> SEQ ID NO 20
<211> LENGTH: 108
<212> TYPE: PRT
<213> ORGANISM: Artificial Sequence
<220> FEATURE:
<223> OTHER INFORMATION: Synthetic Construct

<400> SEQUENCE: 20

Asp Ile Gln Met Thr Gln Ser Pro Ser Ser Leu Ser Ala Ser Val Gly
 1               5                  10                  15

Asp Arg Val Thr Ile Thr Cys Arg Thr Ser Gly Asn Ile His Asn Tyr
             20                  25                  30

Leu Thr Trp Tyr Gln Gln Lys Pro Gly Lys Ala Pro Gln Leu Leu Ile
         35                  40                  45

Tyr Asn Ala Lys Thr Leu Ala Asp Gly Val Pro Ser Arg Phe Ser Gly
     50                  55                  60

Ser Gly Ser Gly Thr Gln Phe Thr Leu Thr Ile Ser Ser Leu Gln Pro
 65                  70                  75                  80

Glu Asp Phe Ala Asn Tyr Tyr Cys Gln His Phe Trp Ser Leu Pro Phe
             85                  90                  95

Thr Phe Gly Gln Gly Thr Lys Val Glu Ile Lys Arg
            100                 105

<210> SEQ ID NO 21
<211> LENGTH: 458
<212> TYPE: DNA
<213> ORGANISM: Artificial Sequence
<220> FEATURE:
<223> OTHER INFORMATION: Oligonucleotide
```

-continued

<400> SEQUENCE: 21

```
gaataaaagc ttgccgccac catggacttt gggctcagct tgattttcct tgtccttact      60
ttaaaaggtg tgcagtgtga ggtgcagctg gtcgagtctg gaggcgggct tgtccagcct     120
ggagggagcc tgcgtctctc ttgtgcagca agcggcttcg acttttcccg ttacgatatg     180
tcctgggtgc ggcaggcacc tgggaagcgc ctggagtggg tggcatacat tagctccgga     240
ggcggctcta catacttccc ggacaccgtc aagggccgtt tcaccatttc ccgggacaat     300
gcaaagaata ccctttacct ccagatgaac tctctccgcg cagaggacac agcaatgtat     360
tactgtgcac ggcagaacaa gaaactgacc tggtttgact actggggaca ggggacccat     420
gtgacagtct cctctgcttc tacaaagggc ccaagaaa                             458
```

<210> SEQ ID NO 22
<211> LENGTH: 414
<212> TYPE: DNA
<213> ORGANISM: Artificial Sequence
<220> FEATURE:
<223> OTHER INFORMATION: Oligonucleotide

<400> SEQUENCE: 22

```
ggatgattcg aagccgccac catgagtgtg ctcactcagg tcctggcgtt gctgctgctg      60
tggcttgcag gtgccagatg tgatatccag atgacccaga gtccaagcag tctctccgcc     120
agcgtaggcg atcgtgtgac tattacctgt cgtaccagtg caacatccta aattacctg     180
acgtggtacc agcaaaaact gggcaaagcc ccgcagctcc tggtctataa cgcgaaaacg     240
ctagcagacg gtgtgccaag ccgtttcagt ggcagtggca cgggtactca gtttacccct     300
caaatttcgt ctctccagcc ggaagatttc gccaattact attgtcagca cttttggagc     360
ctgcctttca ccttcggtca gggcactaaa gtagaaatca aacgtacggc gtgc           414
```

<210> SEQ ID NO 23
<211> LENGTH: 144
<212> TYPE: PRT
<213> ORGANISM: Artificial Sequence
<220> FEATURE:
<223> OTHER INFORMATION: Synthetic Construct

<400> SEQUENCE: 23

```
Met Asp Phe Gly Leu Ser Leu Ile Phe Leu Val Leu Thr Leu Lys Gly
1               5                   10                  15
Val Gln Cys Glu Val Gln Leu Val Glu Ser Gly Gly Gly Leu Val Gln
            20                  25                  30
Pro Gly Gly Ser Leu Arg Leu Ser Cys Ala Ala Ser Gly Phe Asp Phe
        35                  40                  45
Ser Arg Tyr Asp Met Ser Trp Val Arg Gln Ala Pro Gly Lys Arg Leu
    50                  55                  60
Glu Trp Val Ala Tyr Ile Ser Ser Gly Gly Ser Thr Tyr Phe Pro
65                  70                  75                  80
Asp Thr Val Lys Gly Arg Phe Thr Ile Ser Arg Asp Asn Ala Lys Asn
                85                  90                  95
Thr Leu Tyr Leu Gln Met Asn Ser Leu Arg Ala Glu Asp Thr Ala Met
            100                 105                 110
Tyr Tyr Cys Ala Arg Gln Asn Lys Lys Leu Thr Trp Phe Asp Tyr Trp
        115                 120                 125
Gly Gln Gly Thr Leu Val Thr Val Ser Ser Ala Ser Thr Lys Gly Pro
    130                 135                 140
```

<210> SEQ ID NO 24
<211> LENGTH: 129
<212> TYPE: PRT
<213> ORGANISM: Artificial Sequence
<220> FEATURE:
<223> OTHER INFORMATION: Synthetic Construct

<400> SEQUENCE: 24

```
Met Ser Val Leu Thr Gln Val Leu Ala Leu Leu Leu Trp Leu Ala
1               5                   10                  15

Gly Ala Arg Cys Asp Ile Gln Met Thr Gln Ser Pro Ser Ser Leu Ser
            20                  25                  30

Ala Ser Val Gly Asp Arg Val Thr Ile Thr Cys Arg Thr Ser Gly Asn
        35                  40                  45

Ile His Asn Tyr Leu Thr Trp Tyr Gln Gln Lys Leu Gly Lys Ala Pro
    50                  55                  60

Gln Leu Leu Val Tyr Asn Ala Lys Thr Leu Ala Asp Gly Val Pro Ser
65                  70                  75                  80

Arg Phe Ser Gly Ser Gly Ser Gly Thr Gln Phe Thr Leu Thr Ile Ser
                85                  90                  95

Ser Leu Gln Pro Glu Asp Phe Ala Asn Tyr Tyr Cys Gln His Phe Trp
            100                 105                 110

Ser Leu Pro Phe Thr Phe Gly Gln Gly Thr Lys Val Glu Ile Lys Arg
        115                 120                 125

Thr
```

<210> SEQ ID NO 25
<211> LENGTH: 21
<212> TYPE: DNA
<213> ORGANISM: Artificial Sequence
<220> FEATURE:
<223> OTHER INFORMATION: Oligonucleotide

<400> SEQUENCE: 25
gaataaaagc ttgccgccac c                                         21

<210> SEQ ID NO 26
<211> LENGTH: 22
<212> TYPE: DNA
<213> ORGANISM: Artificial Sequence
<220> FEATURE:
<223> OTHER INFORMATION: Oligonucleotide

<400> SEQUENCE: 26
tttcttgggc cctttgtaga ag                                        22

<210> SEQ ID NO 27
<211> LENGTH: 54
<212> TYPE: DNA
<213> ORGANISM: Artificial Sequence
<220> FEATURE:
<223> OTHER INFORMATION: Oligonucleotide

<400> SEQUENCE: 27
atggactttg ggctcagctt gattttcctt gtccttactt taaaaggtgt gcag      54

<210> SEQ ID NO 28
<211> LENGTH: 54
<212> TYPE: DNA
<213> ORGANISM: Artificial Sequence
<220> FEATURE:
<223> OTHER INFORMATION: Oligonucleotide

<400> SEQUENCE: 28
tgtgaggtgc agctggtcga gtctggaggc gggcttgtcc agcctggagg gagc    54

<210> SEQ ID NO 29
<211> LENGTH: 54
<212> TYPE: DNA
<213> ORGANISM: Artificial Sequence
<220> FEATURE:
<223> OTHER INFORMATION: Oligonucleotide

<400> SEQUENCE: 29
ctgcgtctct cttgtgcagc aagcggcttc gactttccc gttacgatat gtcc    54

<210> SEQ ID NO 30
<211> LENGTH: 54
<212> TYPE: DNA
<213> ORGANISM: Artificial Sequence
<220> FEATURE:
<223> OTHER INFORMATION: Oligonucleotide

<400> SEQUENCE: 30
tgggtgcggc aggcacctgg aagcgcctg gagtgggtgg catacattag ctcc    54

<210> SEQ ID NO 31
<211> LENGTH: 54
<212> TYPE: DNA
<213> ORGANISM: Artificial Sequence
<220> FEATURE:
<223> OTHER INFORMATION: Oligonucleotide

<400> SEQUENCE: 31
ggaggcggct ctacatactt cccggacacc gtcaagggcc gtttcaccat ttcc    54

<210> SEQ ID NO 32
<211> LENGTH: 54
<212> TYPE: DNA
<213> ORGANISM: Artificial Sequence
<220> FEATURE:
<223> OTHER INFORMATION: Oligonucleotide

<400> SEQUENCE: 32
cgggacaatg caaagaatac cctttacctc cagatgaact ctctccgcgc agag    54

<210> SEQ ID NO 33
<211> LENGTH: 54
<212> TYPE: DNA
<213> ORGANISM: Artificial Sequence
<220> FEATURE:
<223> OTHER INFORMATION: Oligonucleotide

<400> SEQUENCE: 33
gacacagcaa tgtattactg tgcacggcag aacaagaaac tgacctggtt tgac    54

<210> SEQ ID NO 34
<211> LENGTH: 59
<212> TYPE: DNA
<213> ORGANISM: Artificial Sequence
<220> FEATURE:
<223> OTHER INFORMATION: Oligonucleotide

<400> SEQUENCE: 34
tactggggac aggggaccct tgtgacagtc tcctctgctt ctacaaaggg cccaagaaa    59

<210> SEQ ID NO 35
<211> LENGTH: 58
<212> TYPE: DNA
<213> ORGANISM: Artificial Sequence

```
<220> FEATURE:
<223> OTHER INFORMATION: Oligonucleotide

<400> SEQUENCE: 35
cagaggagac tgtcacaagg gtcccctgtc cccagtagtc aaaccaggtc agtttctt      58

<210> SEQ ID NO 36
<211> LENGTH: 54
<212> TYPE: DNA
<213> ORGANISM: Artificial Sequence
<220> FEATURE:
<223> OTHER INFORMATION: Oligonucleotide

<400> SEQUENCE: 36
gttctgccgt gcacagtaat acattgctgt gtcctctgcg cggagagagt tcat          54

<210> SEQ ID NO 37
<211> LENGTH: 54
<212> TYPE: DNA
<213> ORGANISM: Artificial Sequence
<220> FEATURE:
<223> OTHER INFORMATION: Oligonucleotide

<400> SEQUENCE: 37
ctggaggtaa agggtattct ttgcattgtc ccgggaaatg gtgaaacggc cctt          54

<210> SEQ ID NO 38
<211> LENGTH: 54
<212> TYPE: DNA
<213> ORGANISM: Artificial Sequence
<220> FEATURE:
<223> OTHER INFORMATION: Oligonucleotide

<400> SEQUENCE: 38
gacggtgtcc gggaagtatg tagagccgcc tccggagcta atgtatgcca ccca          54

<210> SEQ ID NO 39
<211> LENGTH: 54
<212> TYPE: DNA
<213> ORGANISM: Artificial Sequence
<220> FEATURE:
<223> OTHER INFORMATION: Oligonucleotide

<400> SEQUENCE: 39
ctccaggcgc ttcccaggtg cctgccgcac ccaggacata tcgtaacggg aaaa          54

<210> SEQ ID NO 40
<211> LENGTH: 54
<212> TYPE: DNA
<213> ORGANISM: Artificial Sequence
<220> FEATURE:
<223> OTHER INFORMATION: Oligonucleotide

<400> SEQUENCE: 40
gtcgaagccg cttgctgcac aagagagacg caggctccct ccaggctgga caag          54

<210> SEQ ID NO 41
<211> LENGTH: 54
<212> TYPE: DNA
<213> ORGANISM: Artificial Sequence
<220> FEATURE:
<223> OTHER INFORMATION: Oligonucleotide

<400> SEQUENCE: 41
cccgcctcca gactcgacca gctgcacctc acactgcaca cctttaaag taag           54
```

```
<210> SEQ ID NO 42
<211> LENGTH: 54
<212> TYPE: DNA
<213> ORGANISM: Artificial Sequence
<220> FEATURE:
<223> OTHER INFORMATION: Oligonucleotide

<400> SEQUENCE: 42
gacaaggaaa atcaagctga gcccaaagtc catggtggcg gcaagctttt attc         54

<210> SEQ ID NO 43
<211> LENGTH: 20
<212> TYPE: DNA
<213> ORGANISM: Artificial Sequence
<220> FEATURE:
<223> OTHER INFORMATION: Oligonucleotide

<400> SEQUENCE: 43
ggatgattcg aagccgccac                                                20

<210> SEQ ID NO 44
<211> LENGTH: 21
<212> TYPE: DNA
<213> ORGANISM: Artificial Sequence
<220> FEATURE:
<223> OTHER INFORMATION: Oligonucleotide

<400> SEQUENCE: 44
gcacgccgta cgtttgattt c                                              21

<210> SEQ ID NO 45
<211> LENGTH: 55
<212> TYPE: DNA
<213> ORGANISM: Artificial Sequence
<220> FEATURE:
<223> OTHER INFORMATION: Oligonucleotide

<400> SEQUENCE: 45
catgagtgtg ctcactcagg tcctggcgtt gctgctgctg tggcttgcag gtgcc         55

<210> SEQ ID NO 46
<211> LENGTH: 57
<212> TYPE: DNA
<213> ORGANISM: Artificial Sequence
<220> FEATURE:
<223> OTHER INFORMATION: Oligonucleotide

<400> SEQUENCE: 46
agatgtgata tccagatgac ccagagtcca agcagtctct ccgccagcgt aggcgat       57

<210> SEQ ID NO 47
<211> LENGTH: 57
<212> TYPE: DNA
<213> ORGANISM: Artificial Sequence
<220> FEATURE:
<223> OTHER INFORMATION: Oligonucleotide

<400> SEQUENCE: 47
cgtgtgacta ttacctgtcg taccagtggc aacatccata attacctgac gtggtac       57

<210> SEQ ID NO 48
<211> LENGTH: 57
<212> TYPE: DNA
<213> ORGANISM: Artificial Sequence
<220> FEATURE:
<223> OTHER INFORMATION: Oligonucleotide

<400> SEQUENCE: 48
```

```
cagcaaaaac tgggcaaagc cccgcagctc ctggtctata acgcgaaaac gctagca      57
```

<210> SEQ ID NO 49
<211> LENGTH: 57
<212> TYPE: DNA
<213> ORGANISM: Artificial Sequence
<220> FEATURE:
<223> OTHER INFORMATION: Oligonucleotide

<400> SEQUENCE: 49

```
gacggtgtgc caagccgttt cagtggcagt ggcagcggta ctcagtttac cctcaca      57
```

<210> SEQ ID NO 50
<211> LENGTH: 57
<212> TYPE: DNA
<213> ORGANISM: Artificial Sequence
<220> FEATURE:
<223> OTHER INFORMATION: Oligonucleotide

<400> SEQUENCE: 50

```
atttcgtctc tccagccgga agatttcgcc aattactatt gtcagcactt ttggagc      57
```

<210> SEQ ID NO 51
<211> LENGTH: 54
<212> TYPE: DNA
<213> ORGANISM: Artificial Sequence
<220> FEATURE:
<223> OTHER INFORMATION: Oligonucleotide

<400> SEQUENCE: 51

```
ctgcctttca ccttcggtca gggcactaaa gtagaaatca aacgtacggc gtgc         54
```

<210> SEQ ID NO 52
<211> LENGTH: 54
<212> TYPE: DNA
<213> ORGANISM: Artificial Sequence
<220> FEATURE:
<223> OTHER INFORMATION: Oligonucleotide

<400> SEQUENCE: 52

```
tactttagtg ccctgaccga aggtgaaagg caggctccaa aagtgctgac aata         54
```

<210> SEQ ID NO 53
<211> LENGTH: 57
<212> TYPE: DNA
<213> ORGANISM: Artificial Sequence
<220> FEATURE:
<223> OTHER INFORMATION: Oligonucleotide

<400> SEQUENCE: 53

```
gtaattggcg aaatcttccg gctggagaga cgaaattgtg agggtaaact gagtacc      57
```

<210> SEQ ID NO 54
<211> LENGTH: 57
<212> TYPE: DNA
<213> ORGANISM: Artificial Sequence
<220> FEATURE:
<223> OTHER INFORMATION: Oligonucleotide

<400> SEQUENCE: 54

```
gctgccactg ccactgaaac ggcttggcac accgtctgct agcgttttcg cgttata      57
```

<210> SEQ ID NO 55
<211> LENGTH: 57
<212> TYPE: DNA
<213> ORGANISM: Artificial Sequence

```
<220> FEATURE:
<223> OTHER INFORMATION: Oligonucleotide

<400> SEQUENCE: 55
gaccaggagc tgcggggctt tgcccagttt ttgctggtac cacgtcaggt aattatg       57

<210> SEQ ID NO 56
<211> LENGTH: 57
<212> TYPE: DNA
<213> ORGANISM: Artificial Sequence
<220> FEATURE:
<223> OTHER INFORMATION: Oligonucleotide

<400> SEQUENCE: 56
gatgttgcca ctggtacgac aggtaatagt cacacgatcg cctacgctgg cggagag       57

<210> SEQ ID NO 57
<211> LENGTH: 57
<212> TYPE: DNA
<213> ORGANISM: Artificial Sequence
<220> FEATURE:
<223> OTHER INFORMATION: Oligonucleotide

<400> SEQUENCE: 57
actgcttgga ctctgggtca tctggatatc acatctggca cctgcaagcc acagcag       57

<210> SEQ ID NO 58
<211> LENGTH: 54
<212> TYPE: DNA
<213> ORGANISM: Artificial Sequence
<220> FEATURE:
<223> OTHER INFORMATION: Oligonucleotide

<400> SEQUENCE: 58
cagcaacgcc aggacctgag tgagcacact catggtggcg gcttcgaatc atcc          54

<210> SEQ ID NO 59
<211> LENGTH: 51
<212> TYPE: DNA
<213> ORGANISM: Artificial Sequence
<220> FEATURE:
<223> OTHER INFORMATION: Oligonucleotide

<400> SEQUENCE: 59
cagcaaaaac cgggcaaagc cccgcagctc ctggtctata acgcgaaaac g             51

<210> SEQ ID NO 60
<211> LENGTH: 21
<212> TYPE: PRT
<213> ORGANISM: Artificial Sequence
<220> FEATURE:
<223> OTHER INFORMATION: Synthetic Construct

<400> SEQUENCE: 60

Trp Tyr Gln Gln Lys Pro Gly Lys Ala Pro Gln Leu Leu Val Tyr Asn
1               5                   10                  15

Ala Lys Thr Leu Ala
            20

<210> SEQ ID NO 61
<211> LENGTH: 51
<212> TYPE: DNA
<213> ORGANISM: Artificial Sequence
<220> FEATURE:
<223> OTHER INFORMATION: Oligonucleotide

<400> SEQUENCE: 61
```
cagcaaaaac cgggcaaagc cccgcagctc ctgatctata acgcgaaaac g       51

<210> SEQ ID NO 62
<211> LENGTH: 21
<212> TYPE: PRT
<213> ORGANISM: Artificial Sequence
<220> FEATURE:
<223> OTHER INFORMATION: Synthetic Construct

<400> SEQUENCE: 62

Trp Tyr Gln Gln Lys Pro Gly Lys Ala Pro Gln Leu Leu Ile Tyr Asn
1               5                   10                  15

Ala Lys Thr Leu Ala
            20

<210> SEQ ID NO 63
<211> LENGTH: 48
<212> TYPE: DNA
<213> ORGANISM: Artificial Sequence
<220> FEATURE:
<223> OTHER INFORMATION: Oligonucleotide

<400> SEQUENCE: 63
cctgggaagg gcctggagtg ggtggcatac attagctccg gaggcggc             48

<210> SEQ ID NO 64
<211> LENGTH: 48
<212> TYPE: DNA
<213> ORGANISM: Artificial Sequence
<220> FEATURE:
<223> OTHER INFORMATION: Oligonucleotide

<400> SEQUENCE: 64
ggacccttcc cggacctcac ccaccgtatg taatcgaggc ctccgccg              48

<210> SEQ ID NO 65
<211> LENGTH: 16
<212> TYPE: PRT
<213> ORGANISM: Artificial Sequence
<220> FEATURE:
<223> OTHER INFORMATION: Synthetic Construct

<400> SEQUENCE: 65

Pro Gly Lys Gly Leu Glu Trp Val Ala Tyr Ile Ser Ser Gly Gly Gly
1               5                   10                  15

<210> SEQ ID NO 66
<211> LENGTH: 54
<212> TYPE: DNA
<213> ORGANISM: Artificial Sequence
<220> FEATURE:
<223> OTHER INFORMATION: Oligonucleotide

<400> SEQUENCE: 66
gacacagcag tgtattactg tgcacggcag aacaagaaac tgacctggtt tgac       54

<210> SEQ ID NO 67
<211> LENGTH: 54
<212> TYPE: DNA
<213> ORGANISM: Artificial Sequence
<220> FEATURE:
<223> OTHER INFORMATION: Oligonucleotide

<400> SEQUENCE: 67
ctgtgtcgtc acataatgac acgtgccgtc ttgttctttg actggaccaa actg       54

```
<210> SEQ ID NO 68
<211> LENGTH: 18
<212> TYPE: PRT
<213> ORGANISM: Artificial Sequence
<220> FEATURE:
<223> OTHER INFORMATION: Synthetic Construct

<400> SEQUENCE: 68

Asp Thr Ala Val Tyr Tyr Cys Ala Arg Gln Asn Lys Lys Leu Thr Trp
1               5                   10                  15

Phe Asp

<210> SEQ ID NO 69
<211> LENGTH: 2050
<212> TYPE: DNA
<213> ORGANISM: Artificial Sequence
<220> FEATURE:
<223> OTHER INFORMATION: Oligonucleotide

<400> SEQUENCE: 69
aattctcatg tttgacagct tatcatcgac tgcacggtgc accaatgctt ctggcgtcag     60
gcagccatcg gaagctgtgg tatggctgtg caggtcgtaa atcactgcat aattcgtgtc    120
gctcaaggcg cactcccgtt ctggataatg ttttttgcgc cgacatcata acggttctgg    180
caaatattct gaaatgagct gttgacaatt aatcatcggc tcgtataatg tgtggaattg    240
tgagcggata caatttcac acaggaaaca gcgatgagct ggctgcagg tcgagttcta      300 gataacgagg cgtaaaaaat gaaaagaca gctatcgcaa ttgcagtggc cttggctggt     360
ttcgctaccg tagcgcaagc tgatatccag atgacccaga gtccaagcag tctctccgcc    420
agcgtaggcg atcgtgtgac tattacctgt cgtaccagtg caacatcca taattacctg     480 acgtggtacc agcaaaaacc gggcaaagcc ccgcagctcc tgatctataa cgcgaaaacg    540
ctagcagacg gtgtgccaag ccgtttcagt ggcagtggca gcggtactca gtttacccctc   600 acaatttcgt ctctccagcc ggaagatttc gccaattact attgtcagca cttttggagc    660
ctgcctttca ccttcggtca gggcactaaa gtagaaatca aacgtacggt agcggcccca    720
tctgtcttca tcttcccgcc atctgatgag cagttgaaat ctggaactgc ctctgttgtg    780
tgcctgctga ataacttcta tcccagagag gccaaagtac agtggaaggt ggataacgcc    840
ctccaatcgg gtaactccca ggagagtgtc acagagcagg acagcaagga cagcacctac    900
agcctcagca gcaccctgac gctgagcaaa gcagactacg agaaacacaa agtctacgcc    960
tgcgaagtca cccatcaggg cctgagctca ccagtaacaa aaagttttaa tagaggggag   1020
tgttaaaatg aagaagactg ctatagcaat tgcagtggcg ctagctggtt tcgccaccgt   1080
ggcgcaagct gaggttcagc tggtcgagtc tggaggcggg cttgtccagc ctggagggag   1140
cctgcgtctc tcttgtgcag caagcggctt cgacttttcc cgttacgata tgtcctgggt   1200
gcggcaggca cctgggaagc gcctggagtg ggtggcatac attagctccg gaggcggctc   1260
tacatacttc ccggacaccg tcaagggccg tttcaccatt tcccgggaca atgcaaagaa   1320
taccctttac ctccagatga actctctccg cgcagaggac acagcagtgt attactgtgc   1380
acggcagaac aagaaactga cctggtttga ctactgggga caggggaccc ttgtgacagt   1440
ctcctctgct tctacaaagg gcccatcggt cttccccctg gcaccctcct ccaagagcac   1500
ctctgggggc acagcggccc tgggctgcct ggtcaaggac tacttccccg aaccggtgac   1560
ggtgtcgtgg aactcaggcg ccctgaccag cggcgtgcac accttcccgg ctgtcctaca   1620
gtcctcagga ctctactccc tcagcagcgt ggtgaccgtg ccctccagca gcttgggcac   1680
```

```
ccagacctac atctgcaacg tgaatcacaa gcccagcaac accaaggtcg acaagaaagt   1740
tgagcccaaa tcttgtgaca aaactcacac atgcgccgcg tgatgaggat ccaagcttgc   1800
ggccgcgaat tcactggccg tcgttttaca acgtcgtgac tgggaaaacc ctggcgttac   1860
ccaacttaat cgccttgcag cacatccccc tttcgccagc tcgcgtaata gcgaagaggc   1920
ccgcaccgat cgcccttccc aacagttgcg cagcctgaat ggcgaatggc gcctgatgcg   1980
gtattttctc cttacgcatc tgtgcggtat ttcacaccgc ataaattccc tgttttggcg   2040
gatgagagaa                                                         2050
```

<210> SEQ ID NO 70
<211> LENGTH: 235
<212> TYPE: PRT
<213> ORGANISM: Artificial Sequence
<220> FEATURE:
<223> OTHER INFORMATION: Synthetic Construct

<400> SEQUENCE: 70

```
Met Lys Lys Thr Ala Ile Ala Ile Ala Val Ala Leu Ala Gly Phe Ala
1               5                   10                  15

Thr Val Ala Gln Ala Asp Ile Gln Met Thr Gln Ser Pro Ser Ser Leu
            20                  25                  30

Ser Ala Ser Val Gly Asp Arg Val Thr Ile Thr Cys Arg Thr Ser Gly
        35                  40                  45

Asn Ile His Asn Tyr Leu Thr Trp Tyr Gln Gln Lys Pro Gly Lys Ala
    50                  55                  60

Pro Gln Leu Leu Ile Tyr Asn Ala Lys Thr Leu Ala Asp Gly Val Pro
65                  70                  75                  80

Ser Arg Phe Ser Gly Ser Gly Ser Gly Thr Gln Phe Thr Leu Thr Ile
                85                  90                  95

Ser Ser Leu Gln Pro Glu Asp Phe Ala Asn Tyr Tyr Cys Gln His Phe
            100                 105                 110

Trp Ser Leu Pro Phe Thr Phe Gly Gln Gly Thr Lys Val Glu Ile Lys
        115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235
```

<210> SEQ ID NO 71
<211> LENGTH: 251
<212> TYPE: PRT
<213> ORGANISM: Artificial Sequence
<220> FEATURE:
<223> OTHER INFORMATION: Synthetic Construct

<400> SEQUENCE: 71

```
Met Lys Lys Thr Ala Ile Ala Ile Ala Val Ala Leu Ala Gly Phe Ala
1               5                   10                  15

Thr Val Ala Gln Ala Glu Val Gln Leu Val Glu Ser Gly Gly Gly Leu
                20                  25                  30

Val Gln Pro Gly Gly Ser Leu Arg Leu Ser Cys Ala Ala Ser Gly Phe
            35                  40                  45

Asp Phe Ser Arg Tyr Asp Met Ser Trp Val Arg Gln Ala Pro Gly Lys
        50                  55                  60

Arg Leu Glu Trp Val Ala Tyr Ile Ser Ser Gly Gly Ser Thr Tyr
65                  70                  75                  80

Phe Pro Asp Thr Val Lys Gly Arg Phe Thr Ile Ser Arg Asp Asn Ala
                85                  90                  95

Lys Asn Thr Leu Tyr Leu Gln Met Asn Ser Leu Arg Ala Glu Asp Thr
            100                 105                 110

Ala Val Tyr Tyr Cys Ala Arg Gln Asn Lys Lys Leu Thr Trp Phe Asp
        115                 120                 125

Tyr Trp Gly Gln Gly Thr Leu Val Thr Val Ser Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
    210                 215                 220

Val Asn His Lys Pro Ser Asn Thr Lys Val Asp Lys Lys Val Glu Pro
225                 230                 235                 240

Lys Ser Cys Asp Lys Thr His Thr Cys Ala Ala
                245                 250

<210> SEQ ID NO 72
<211> LENGTH: 59
<212> TYPE: DNA
<213> ORGANISM: Artificial Sequence
<220> FEATURE:
<223> OTHER INFORMATION: Oligonucleotide

<400> SEQUENCE: 72
ctagcgtttt cgcgttatag accaggagct gcggggcttt gcccggtttt tgctggtac      59

<210> SEQ ID NO 73
<211> LENGTH: 59
<212> TYPE: DNA
<213> ORGANISM: Artificial Sequence
<220> FEATURE:
<223> OTHER INFORMATION: Oligonucleotide

<400> SEQUENCE: 73
ctagcgtttt cgcgttatag atcaggagct gcggggcttt gcccggtttt tgctggtac      59

<210> SEQ ID NO 74
<211> LENGTH: 15
<212> TYPE: PRT
<213> ORGANISM: Homo sapiens

<400> SEQUENCE: 74
```

```
Tyr Phe Asp Tyr Trp Gly Gln Gly Thr Leu Val Thr Val Ser Ser
1               5                   10                  15

<210> SEQ ID NO 75
<211> LENGTH: 12
<212> TYPE: PRT
<213> ORGANISM: Homo sapiens

<400> SEQUENCE: 75

Trp Thr Phe Gly Gln Gly Thr Lys Val Glu Ile Lys
1               5                   10
```